(12) United States Patent
Fitch et al.

(10) Patent No.: US 12,178,961 B2
(45) Date of Patent: Dec. 31, 2024

(54) MULTIFUNCTIONAL VENTILATOR INTERFACES

(71) Applicant: Hill-Rom Services PTE. LTD., Singapore (SG)

(72) Inventors: Timothy Fitch, Batesville, IN (US); Tom Westfall, Batesville, IN (US)

(73) Assignee: HILL-ROM SERVICES PTE. LTD., Singapore (SG)

(*) Notice: Subject to any disclaimer, the term of this patent is extended or adjusted under 35 U.S.C. 154(b) by 442 days.

(21) Appl. No.: 17/505,931

(22) Filed: Oct. 20, 2021

(65) Prior Publication Data

US 2022/0126052 A1    Apr. 28, 2022

Related U.S. Application Data

(60) Provisional application No. 63/104,147, filed on Oct. 22, 2020.

(51) Int. Cl.
*A61M 16/08*    (2006.01)
*A61M 16/00*    (2006.01)
(Continued)

(52) U.S. Cl.
CPC .... *A61M 16/0875* (2013.01); *A61M 16/0057* (2013.01); *A61M 16/0096* (2013.01);
(Continued)

(58) Field of Classification Search
CPC .... A61M 16/00–0003; A61M 16/0012; A61M 16/0051; A61M 16/0057;
(Continued)

(56) References Cited

U.S. PATENT DOCUMENTS 266,540 A    10/1882  Small
1,176,146 A    3/1916  Jones
(Continued)

FOREIGN PATENT DOCUMENTS

CN    101888870 A    11/2010
GB    2407043 B    4/2006
(Continued)

OTHER PUBLICATIONS

Chinese Office Action for Chinese Application No. 2021112360258; mailed Jul. 15, 2023.
European Search Report for EP 21 20 4230; mailed Mar. 23, 2022.

*Primary Examiner* — Rachel T Sippel
(74) *Attorney, Agent, or Firm* — Stetina Brunda Garred & Brucker

(57) ABSTRACT

A multifunctional ventilator interface for selectively providing ventilation and continuous oxygen therapy to a patient includes tubing defining a high-pressure gas lumen, a low-pressure gas lumen, and a pressure sensing lumen, a manifold housing defining a gas pathway, a jet pump housing coupled to the manifold housing and defining an entrainment port, a sleeve rotatably engaged to the jet pump housing, and a jet nozzle defining high- and low-pressure jet nozzle outlet ports operative to introduce gas from the high- and low-pressure gas lumens into the gas pathway. The sleeve includes first and second windows selectively alignable with the entrainment port by rotation of the sleeve, the first window configured to allow ambient air to flow into the entrainment port when at least partially aligned therewith, the second window being covered by a one-way valve configured to prevent ambient air from flowing into the entrainment port but to allow exhalation out of the entrainment port when the second window is at least partially aligned therewith.

20 Claims, 13 Drawing Sheets

(51) Int. Cl.
*A61M 16/06* (2006.01)
*A61M 25/00* (2006.01)

(52) U.S. Cl.
CPC .... *A61M 16/0672* (2014.02); *A61M 16/0833* (2014.02); *A61M 25/0026* (2013.01)

(58) Field of Classification Search
CPC ............ A61M 16/0096; A61M 16/021; A61M 16/0666–0683; A61M 16/08; A61M 16/0816; A61M 16/0833; A61M 16/0841; A61M 16/0858; A61M 16/0875–0883; A61M 16/10–101; A61M 16/20; A61M 16/208–209; A61M 2016/0027
See application file for complete search history.

(56) References Cited

U.S. PATENT DOCUMENTS

| | | | |
|---|---|---|---|
| 1,176,886 | A | 3/1916 | George |
| 3,726,275 | A | 4/1973 | Jackson et al. |
| 3,906,996 | A | 9/1975 | Depass et al. |
| 3,913,607 | A | 10/1975 | Price |
| 3,977,432 | A | 8/1976 | Vidal |
| 4,036,253 | A | 7/1977 | Fegan et al. |
| 4,054,133 | A | 10/1977 | Myers |
| 4,796,617 | A | 1/1989 | Matthews et al. |
| 5,099,836 | A | 3/1992 | Rowland et al. |
| 5,301,662 | A | 4/1994 | Bagwell et al. |
| 5,348,000 | A | 9/1994 | Teves |
| 5,572,994 | A | 11/1996 | Smith |
| 5,797,389 | A | 8/1998 | Ryder |
| 6,776,162 | B2 | 8/2004 | Wood |
| 7,007,694 | B2 | 3/2006 | Aylsworth et al. |
| 7,080,645 | B2 | 7/2006 | Genger et al. |
| 7,614,401 | B2 | 11/2009 | Thompson |
| 7,775,210 | B2 | 8/2010 | Schbel et al. |
| 7,866,320 | B2 | 1/2011 | Nichols |
| 8,333,200 | B2 | 12/2012 | Tero |
| 8,677,999 | B2 | 3/2014 | Allum et al. |
| 8,893,720 | B2 | 11/2014 | Cohen |
| 9,038,635 | B2 | 5/2015 | Brambilla |
| 9,132,250 | B2 | 9/2015 | Allum et al. |
| 9,289,568 | B2 | 3/2016 | Dhuper et al. |
| 10,076,619 | B2 | 9/2018 | Sears et al. |
| 10,076,625 | B2 | 9/2018 | Tero |
| 10,076,626 | B2 | 9/2018 | Heck |
| 10,307,552 | B2 | 6/2019 | Bambrilla et al. |
| 2006/0180149 | A1 | 8/2006 | Matarasso |
| 2008/0041393 | A1 | 2/2008 | Bracken |
| 2009/0283097 | A1 | 11/2009 | Niklewski |
| 2015/0034090 | A1 | 2/2015 | Berger et al. |
| 2017/0148440 | A1 | 5/2017 | Coleman |
| 2019/0099570 | A1 | 4/2019 | Brambilla et al. |

FOREIGN PATENT DOCUMENTS

| | | |
|---|---|---|
| WO | 2009052631 A1 | 4/2009 |
| WO | 2010146870 A1 | 12/2010 |
| WO | 2020070712 A1 | 4/2020 |

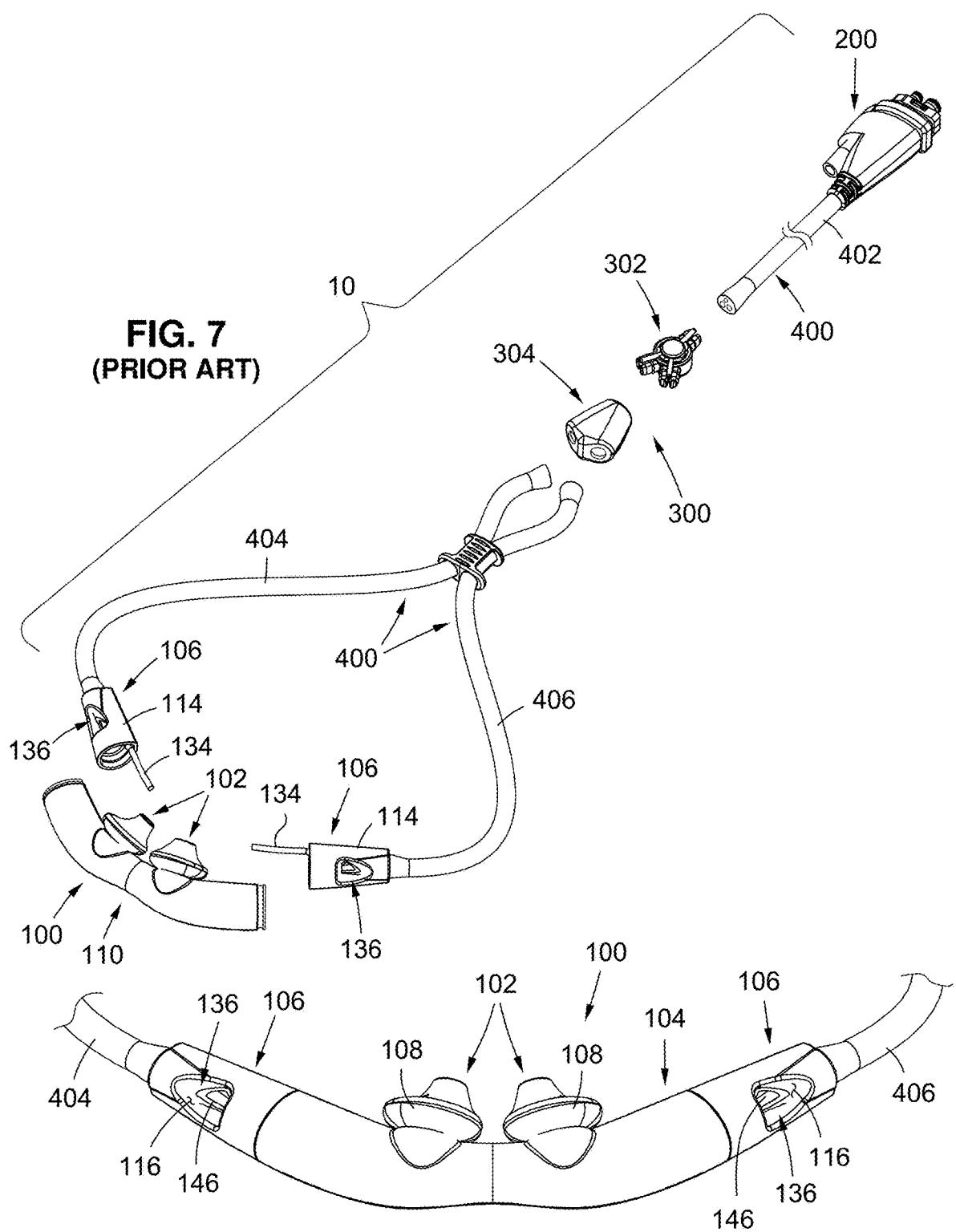

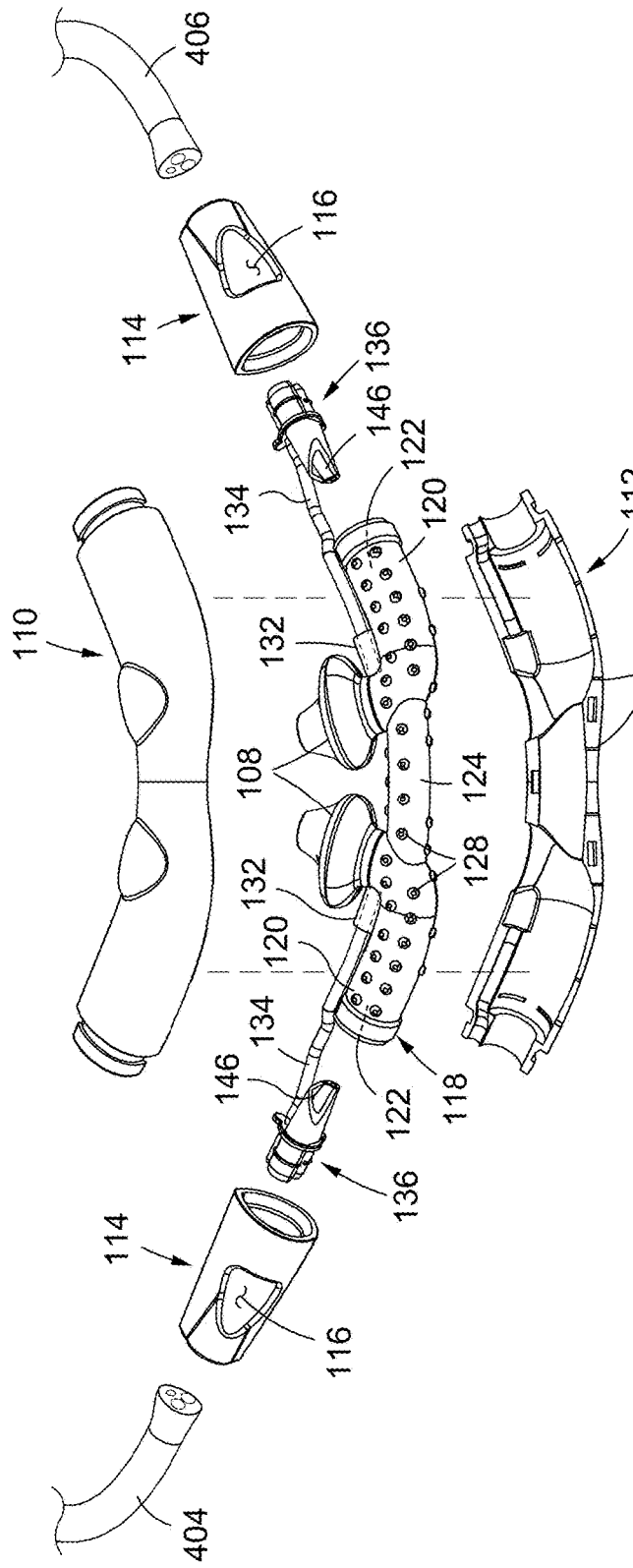
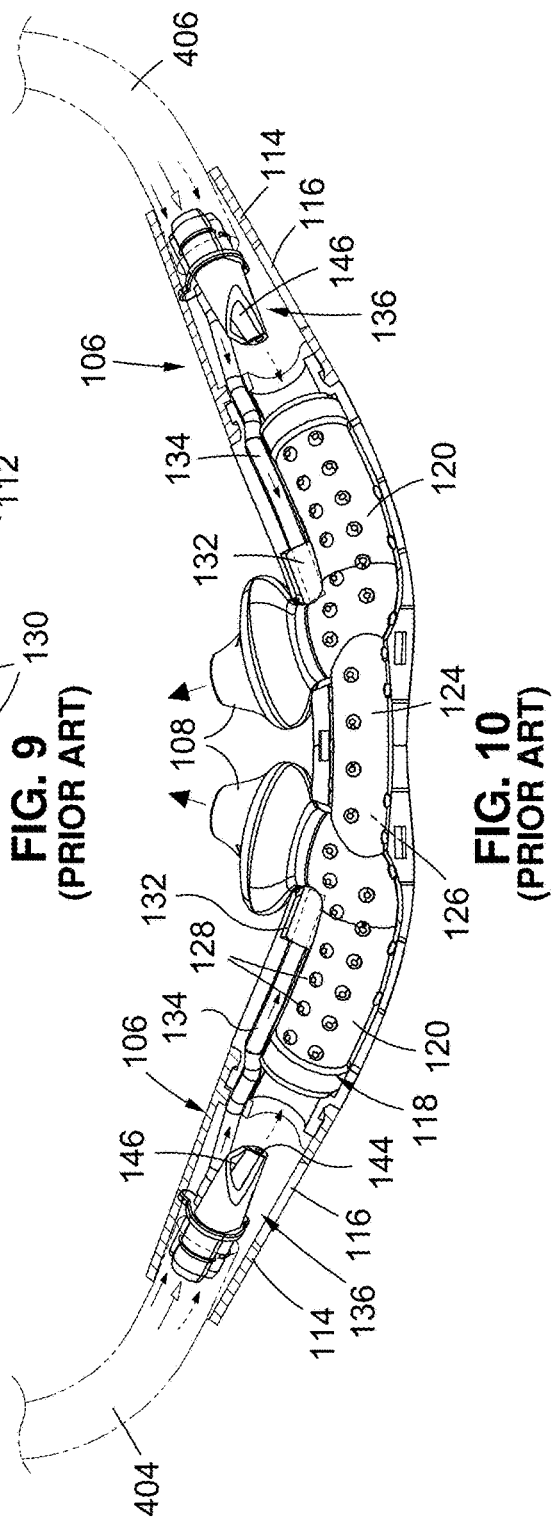
FIG. 9 (PRIOR ART)
FIG. 10 (PRIOR ART)

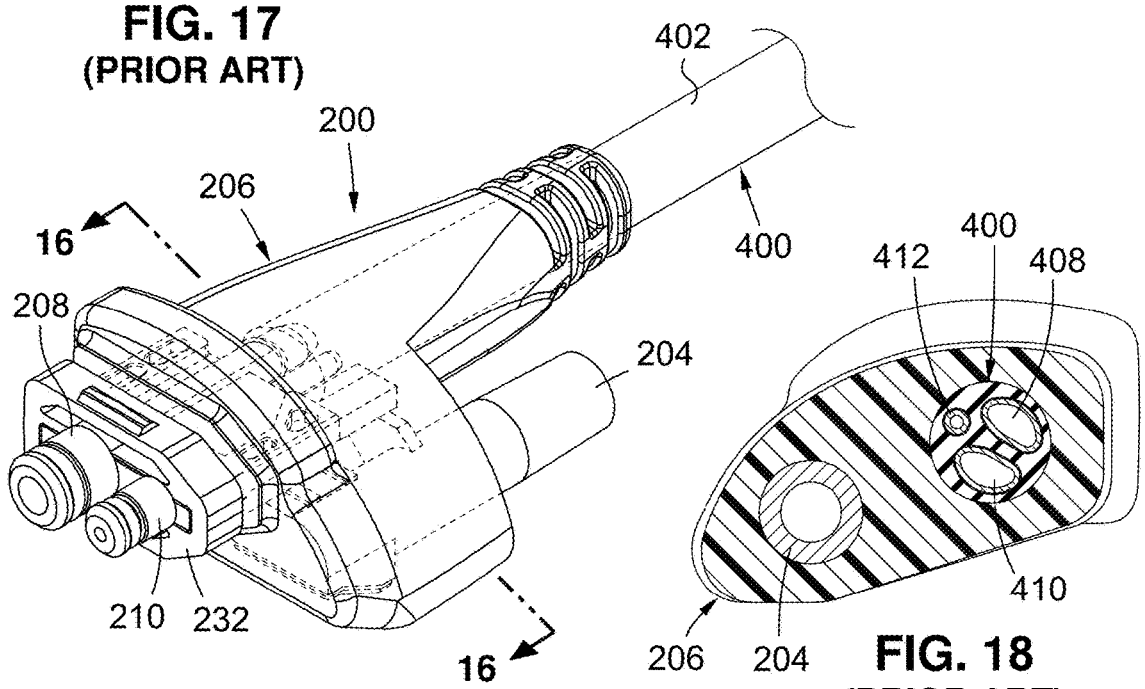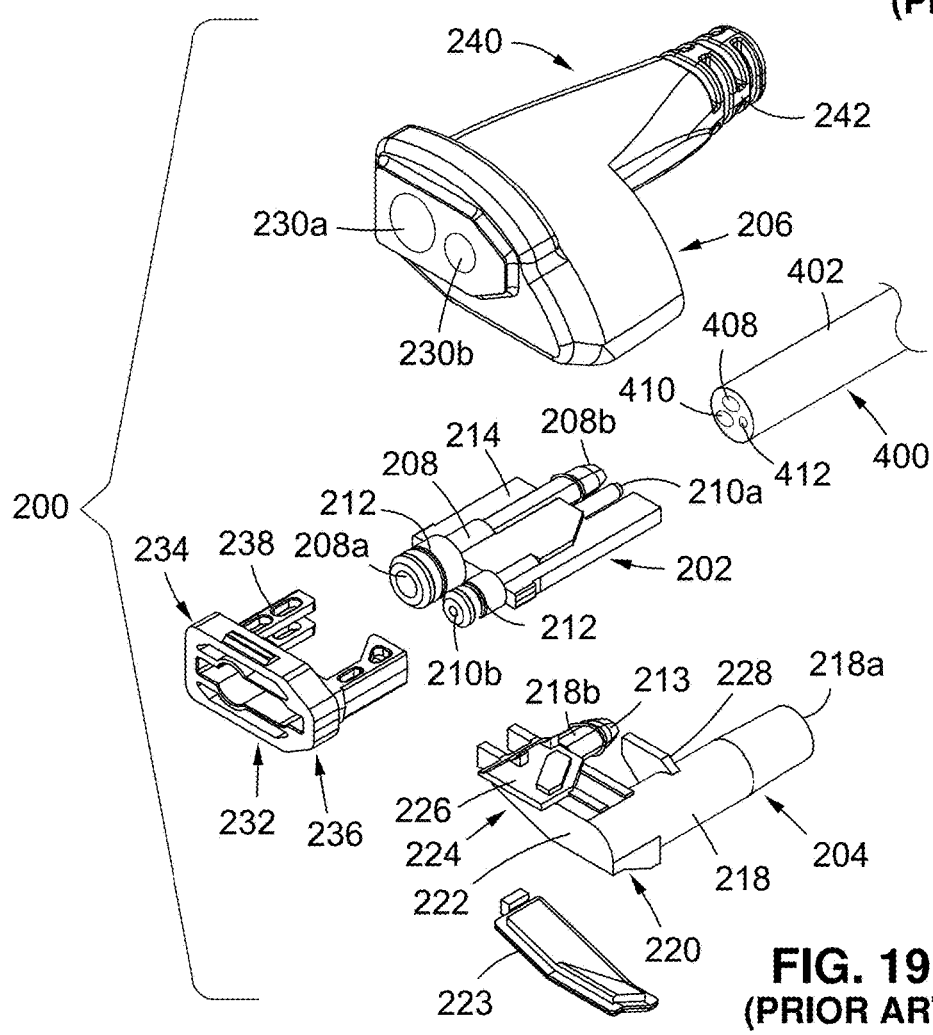

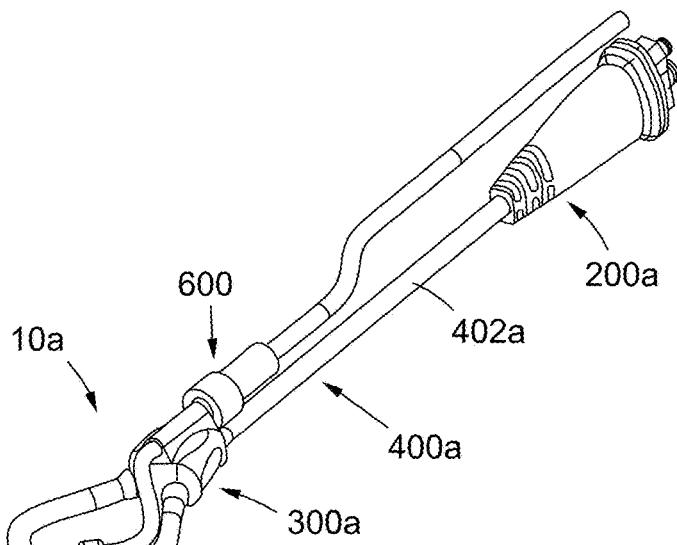
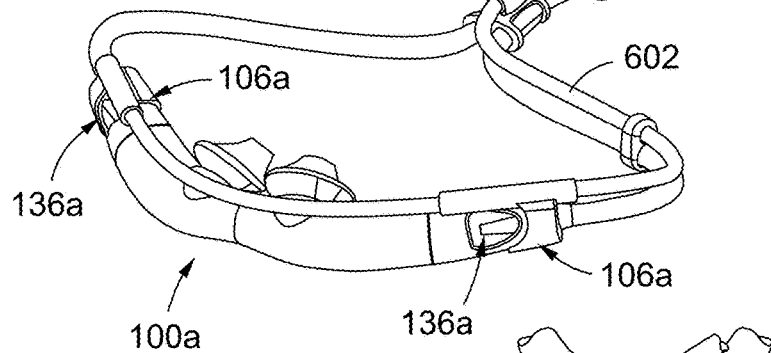
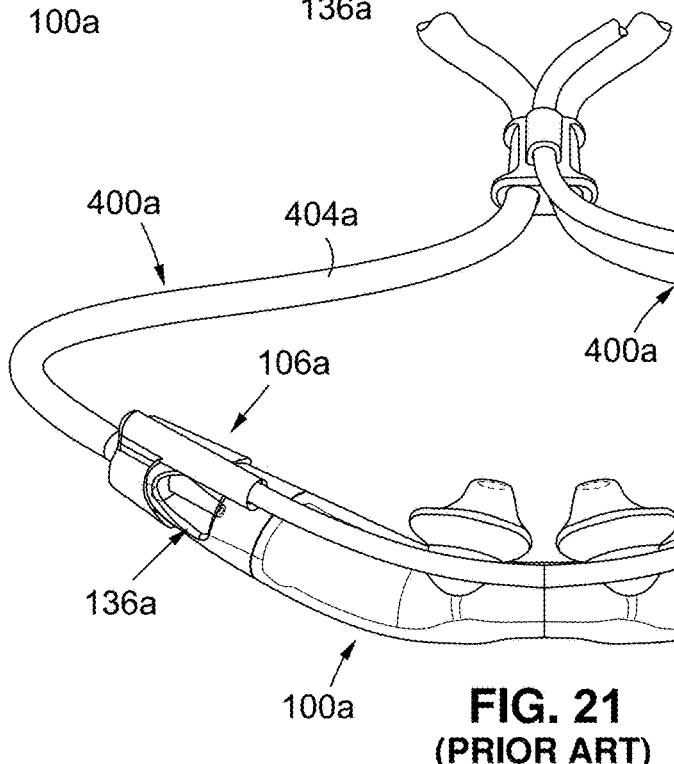
FIG. 20 (PRIOR ART)
FIG. 21 (PRIOR ART)

MULTIFUNCTIONAL VENTILATOR INTERFACES

CROSS-REFERENCE TO RELATED APPLICATIONS

This application relates to and claims the benefit of U.S. Provisional Application No. 63/104,147, filed Oct. 22, 2020 and entitled "MULTIFUNCTIONAL VENTILATOR INTERFACES," the entire contents of which is expressly incorporated herein by reference.

STATEMENT RE: FEDERALLY SPONSORED RESEARCH/DEVELOPMENT

Not Applicable

BACKGROUND

1. Field of the Invention

The present disclosure relates to systems and methods for controlling delivery of a pressurized flow of breathable gas to a patient and, more particularly, to a patient circuit of a ventilation system, such as a non-invasive open ventilation system, wherein the patient circuit may comprise a nasal pillows style patient interface for delivering high pressure air to a patient and incorporating at least one "Venturi effect" jet pump proximal to the patient, a nasal cannula for delivering low pressure oxygen to patient, or a combination of both. The patient circuit may further comprise tri-lumen tubing to facilitate the cooperative engagement of the patient interface(s) to a ventilator of the ventilation system.

2. Description of the Related Art

As is known in the medical arts, mechanical ventilators comprise medical devices that either perform or supplement breathing for patients. The vast majority of contemporary ventilators use positive pressure to deliver gas to the patient's lungs via a patient circuit between the ventilator and the patient. The patient circuit typically consists of one or two large bore tubes that interface to the ventilator on one end, and a patient mask on the other end. In many instances, the patient mask is not provided as part of the ventilation system, and a wide variety of patient masks can be used with any ventilator.

Current ventilators are designed to support either "vented" or "leak" circuits, or "non-vented" or "non-leak" circuits. In vented circuits, the mask or patient interface is provided with an intentional leak, usually in the form of a plurality of vent openings. Ventilators using this configuration are most typically used for less acute clinical requirements, such as the treatment of obstructive sleep apnea or respiratory insufficiency. In non-vented circuits, the patient interface is usually not provided with vent openings. Non-vented circuits can have single limb or dual limb patient circuits, and an exhalation valve. Ventilators using non-vented patient circuits are most typically used for critical care applications.

With particular regard to vented patient circuits, these are used only to carry gas flow from the ventilator to the patient and patient mask and require a patient mask with vent openings. When utilizing vented circuits, the patient inspires fresh gas from the patient circuit, and expires $CO_2$-enriched gas, which is typically purged from the system through the vent openings in the mask. In the vented patient circuit, the ventilator pressurizes the gas to be delivered to the patient inside the ventilator to the intended patient pressure, and then delivers that pressure to the patient through the patient circuit. Very small pressure drops develop through the patient circuit due to gas flow though the small amount of resistance created by the tubing. Some ventilators compensate for this small pressure drop either by mathematical algorithms, or by sensing the tubing pressure more proximal to the patient.

One notable deficiency of certain ventilation systems is that when the breathable gas supplied to the ventilator is air, the ventilator and patient circuit (including the patient interface) of the ventilation system are not well suited for delivering supplemental oxygen to the patient from an oxygen concentrator or other oxygen source. Along these lines, it is known that the maximum outlet from a stationary oxygen concentrator is around 5 l/min of oxygen and 10-15 PSI, whereas certain existing ventilators typically require a minimum of 42 PSI to operate correctly and may require up to 40-45 l/min peak flow to ventilate a patient, depending on the therapy. As a means for addressing this deficiency, some ventilation systems are designed to deliver supplemental oxygen coming from an oxygen concentrator or other oxygen source to the patient via a dedicated port in the patient circuit. See, for example, Applicant's U.S. Patent Application Pub. No. 2019/0099570 published Apr. 4, 2019, the entire contents of which is expressly incorporated herein by reference.

Patients needing oxygen therapy currently have discrete options of, on the one hand, ventilation (e.g. ventilation with supplemental oxygen as described above) and, on the other hand, continuous $O_2$ therapy. In some cases, a patient who is prescribed ventilation may need to switch from ventilation to continuous $O_2$ therapy several times during the course of a single day. This may in turn result in the need for two dedicated ventilation systems which require that the patient switch back and forth between one and the other. For any ventilation system capable of providing both ventilation with supplemental oxygen or oxygen alone, a patient would benefit from a multifunctional ventilator interface that optimizes the delivery of ventilation (with or without supplemental oxygen) and oxygen alone. The patient would also benefit from a multifunctional ventilator interface wherein the functionality thereof in delivering ventilation (with or without supplemental oxygen) and oxygen alone is not compromised in certain use conditions, such as when the patient showers or eats, or during other tasks which may require exertion and increased need for oxygen.

BRIEF SUMMARY

The present disclosure contemplates various methods for overcoming the drawbacks accompanying the related art. One aspect of the embodiments of the present disclosure is a multifunctional ventilator interface for selectively providing ventilation and continuous oxygen therapy to a patient. The multifunctional ventilator interface may comprise a first segment of tubing defining a high-pressure gas lumen, a low-pressure gas lumen, and a pressure sensing lumen that are isolated from each other within the tubing. The multifunctional ventilator interface may also include a manifold housing defining a ventilation gas pathway, a jet pump housing coupled to the manifold housing and defining at least one entrainment port in fluid communication with ambient air, and a jet nozzle cooperatively engaged to the jet pump housing, the jet nozzle defining a high-pressure jet nozzle outlet port operative to introduce gas from the high-pressure gas lumen into the ventilation gas pathway and to facilitate air entrainment through the entrainment port and mixing of the entrained air with the gas concurrently introduced into the ventilation gas pathway. The multifunctional ventilator interface may further comprise a nasal cannula defining a continuous oxygen therapy gas pathway and a second segment of tubing fluidly coupling the low-pressure gas lumen of the first segment of tubing with the continuous oxygen therapy gas pathway of the nasal cannula.

The jet nozzle may define a low-pressure jet nozzle outlet port operative to introduce gas from the low-pressure gas lumen into the ventilation gas pathway. The low-pressure gas lumen may branch from the first segment of tubing to define a first branch that extends within the second segment of tubing and a second branch that continues to the jet nozzle. The multifunctional ventilator interface may comprise a wye connector for branching the low-pressure gas lumen from the first segment of tubing to define the first and second branches. The wye connector may include a switch operative to toggle between blocking the first branch and blocking the second branch.

The low-pressure gas lumen may be bifurcated from the first segment of tubing without branching to extend within the second segment of tubing.

The manifold housing may define a pressure sensing pathway that fluidly communicates with a prescribed region of the ventilation gas pathway and is operative to be fluidly coupled to the pressure sensing lumen.

Another aspect of the embodiments of the present disclosure is a system for selectively providing ventilation and continuous oxygen therapy to a patient. The system may comprise the above multifunctional ventilator interface and a ventilator operable to provide ventilation gas to the jet nozzle via the high-pressure gas lumen of the first segment of tubing.

Another aspect of the embodiments of the present disclosure is a multifunctional ventilator interface for selectively providing ventilation and continuous oxygen therapy to a patient. The multifunctional ventilator interface may comprise a first segment of tubing defining a high-pressure gas lumen, a low-pressure gas lumen, and a pressure sensing lumen that are isolated from each other within the tubing, the first segment of tubing terminating at a first quick connect fitting. The multifunctional ventilator interface may also include a second segment of tubing defining a high-pressure gas lumen and a pressure sensing lumen, with the second segment of tubing terminating in a second quick connect fitting connectable to the first quick connect fitting to fluidly couple the high-pressure gas lumen of the first segment of tubing with the high-pressure gas lumen of the second segment of tubing, and to further fluidly couple the pressure sensing lumen of the first segment of tubing with the pressure sensing lumen of the second segment of tubing. Still further, the multifunctional ventilator interface may include a third segment of tubing defining a low-pressure gas lumen, the third segment of tubing terminating in a third quick connect fitting connectable to the first quick connect fitting in selective substitution for the second quick connect fitting to fluidly couple the low-pressure gas lumen of the first segment of tubing with the low-pressure gas lumen of the third segment of tubing. The multifunctional ventilator interface may further comprise a manifold housing defining a ventilation gas pathway, a jet pump housing coupled to the manifold housing and defining at least one entrainment port in fluid communication with ambient air, and a jet nozzle cooperatively engaged to the jet pump housing, the jet nozzle defining a high-pressure jet nozzle outlet port operative to introduce gas from the high-pressure gas lumen of the second segment of tubing into the ventilation gas pathway and to facilitate air entrainment through the entrainment port and mixing of the entrained air with the gas concurrently introduced into the ventilation gas pathway. The manifold housing may also define a discrete pressure sensing pathway which fluidly communicates with a prescribed region of the ventilation gas pathway as is fluidly coupled to the pressure sensing lumen of the second segment of the tubing. The multifunctional ventilator interface may further comprise a nasal cannula defining a continuous oxygen therapy gas pathway in fluid communication with the low-pressure gas lumen of the third segment of tubing.

The second segment of tubing may define a pressure sensing lumen, and the second quick connect fitting may fluidly couple the pressure sensing lumen of the first segment of tubing with the pressure sensing lumen of the second segment of tubing. The second segment of tubing may define a low-pressure gas lumen, and the second quick connect fitting may fluidly couple the low-pressure gas lumen of the first segment of tubing with the low-pressure gas lumen of the second segment of tubing. The third quick connect fitting may block the high-pressure gas lumen and/or the pressure sensing lumen of the first segment of tubing.

Another aspect of the embodiments of the present disclosure is a system for selectively providing ventilation and continuous oxygen therapy to a patient. The system may comprise the above multifunctional ventilator interface and a ventilator operable to provide ventilation gas to the jet nozzle via the high-pressure gas lumens of the first and second segments of tubing.

Another aspect of the embodiments of the present disclosure is a multifunctional ventilator interface for selectively providing ventilation and continuous oxygen therapy to a patient. The multifunctional ventilator interface may comprise tubing defining a high-pressure gas lumen, a low-pressure gas lumen, and a pressure sensing lumen that are isolated from each other within the tubing. The multifunctional ventilator interface may further comprise a manifold housing defining a gas pathway, a jet pump housing coupled to the manifold housing and defining at least one entrainment port in fluid communication with ambient air, and a jet nozzle cooperatively engaged to the jet pump housing. The jet nozzle may define a high-pressure jet nozzle outlet port operative to introduce gas from the high-pressure gas lumen into the gas pathway and to facilitate air entrainment through the entrainment port and mixing of the entrained air with the gas concurrently introduced into the gas pathway. The jet nozzle may further define a low-pressure jet nozzle outlet port operative to introduce gas from the low-pressure gas lumen into the gas pathway. The manifold housing may also define a discrete pressure sensing pathway which fluidly communicates with a prescribed region of the ventilation gas pathway and is fluidly coupled to the pressure sensing lumen of the tubing. The multifunctional ventilator interface may further comprise a sleeve rotatably engaged to the jet pump housing. In one implementation, the sleeve may include a first window and a second window selectively alignable with the entrainment port by rotation of the sleeve, the first window configured to allow ambient air to flow into the entrainment port, the second window defining a one-way valve configured to prevent ambient air from flowing into the entrainment port but to allow exhalation out of the entrainment port.

The second window may be on the opposite side of the sleeve from the first window.

The sleeve may be prevented from assuming any rotational position in which patient exhalation cannot flow through the entrainment port.

Another aspect of the embodiments of the present disclosure is a system for selectively providing ventilation and continuous oxygen therapy to a patient. The system may comprise the above multifunctional ventilator interface and a ventilator operable to provide ventilation gas to the jet nozzle via the high-pressure gas lumen.

Another aspect of the embodiments of the present disclosure is a multifunctional ventilator interface for selectively providing ventilation and continuous oxygen therapy to a patient. The multifunctional ventilator interface may comprise tubing defining a high-pressure gas lumen, a low-pressure gas lumen, and a pressure sensing lumen that are isolated from each other within the tubing. The multifunctional ventilator interface may further comprise a manifold housing defining a gas pathway, a jet pump housing coupled to the manifold housing and defining a one-way exhaust valve and at least one entrainment port in fluid communication with ambient air, and a jet nozzle cooperatively engaged to the jet pump housing. The jet nozzle may define a high-pressure jet nozzle outlet port operative to introduce gas from the high-pressure gas lumen into the gas pathway and to facilitate air entrainment through the entrainment port and mixing of the entrained air with the gas concurrently introduced into the gas pathway. The jet nozzle may further define a low-pressure jet nozzle outlet port operative to introduce gas from the low-pressure gas lumen into the gas pathway. The multifunctional ventilator interface may further comprise a sleeve rotatably engaged to the jet pump housing, the sleeve including a window selectively alignable with one of the entrainment port and the one-way valve by rotation of the sleeve relative to the jet pump housing, the window being configured to allow ambient air to flow into the entrainment port when at least partially aligned therewith and to allow the one-way exhaust valve to operate when at least partially aligned therewith.

The one-way valve may be on the opposite side of the jet pump housing from the entrainment port.

The sleeve may be prevented from assuming any rotational position in which patient exhalation can flow neither through the entrainment port nor through the one-way exhaust valve.

Another aspect of the embodiments of the present disclosure is a system for selectively providing ventilation and continuous oxygen therapy to a patient. The system may comprise the above multifunctional ventilator interface and a ventilator operable to provide ventilation gas to the jet nozzle via the high-pressure gas lumen.

The present disclosure will be best understood by reference to the following detailed description when read in conjunction with the accompanying drawings.

BRIEF DESCRIPTION OF THE DRAWINGS

The above and other features and advantages of the various embodiments disclosed herein will be better understood with respect to the following description and drawings, in which like numbers refer to like parts throughout, and in which:

FIG. 7 is an exploded view of the patient circuit shown in FIG. 5;

FIG. 8 is a front elevational view of the patient interface included in the patient circuit;

FIG. 9 is an exploded view of the patient interface shown in FIG. 8;

FIG. 10 is a cross-sectional view of the patient circuit shown in FIG. 8;

FIG. 17 is a top perspective view of the primary connector of the patient circuit;

FIG. 18 is an exploded view of the primary connector shown in FIG. 17;

FIG. 19 is a cross-sectional view taken along line 16-16 of FIG. 17;

FIG. 20 is a top perspective view of an alternative embodiment of the patient circuit; and FIG. 21 is a front perspective view of the alternative patient circuit shown in FIG. 20.

DETAILED DESCRIPTION

The present disclosure encompasses various embodiments of systems and methods for providing a multifunctional ventilator interface that is selectively adaptable for continuous $O_2$ therapy. The detailed description set forth below in connection with the appended drawings is intended as a description of several currently contemplated embodiments and is not intended to represent the only form in which the disclosed invention may be developed or utilized.

The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
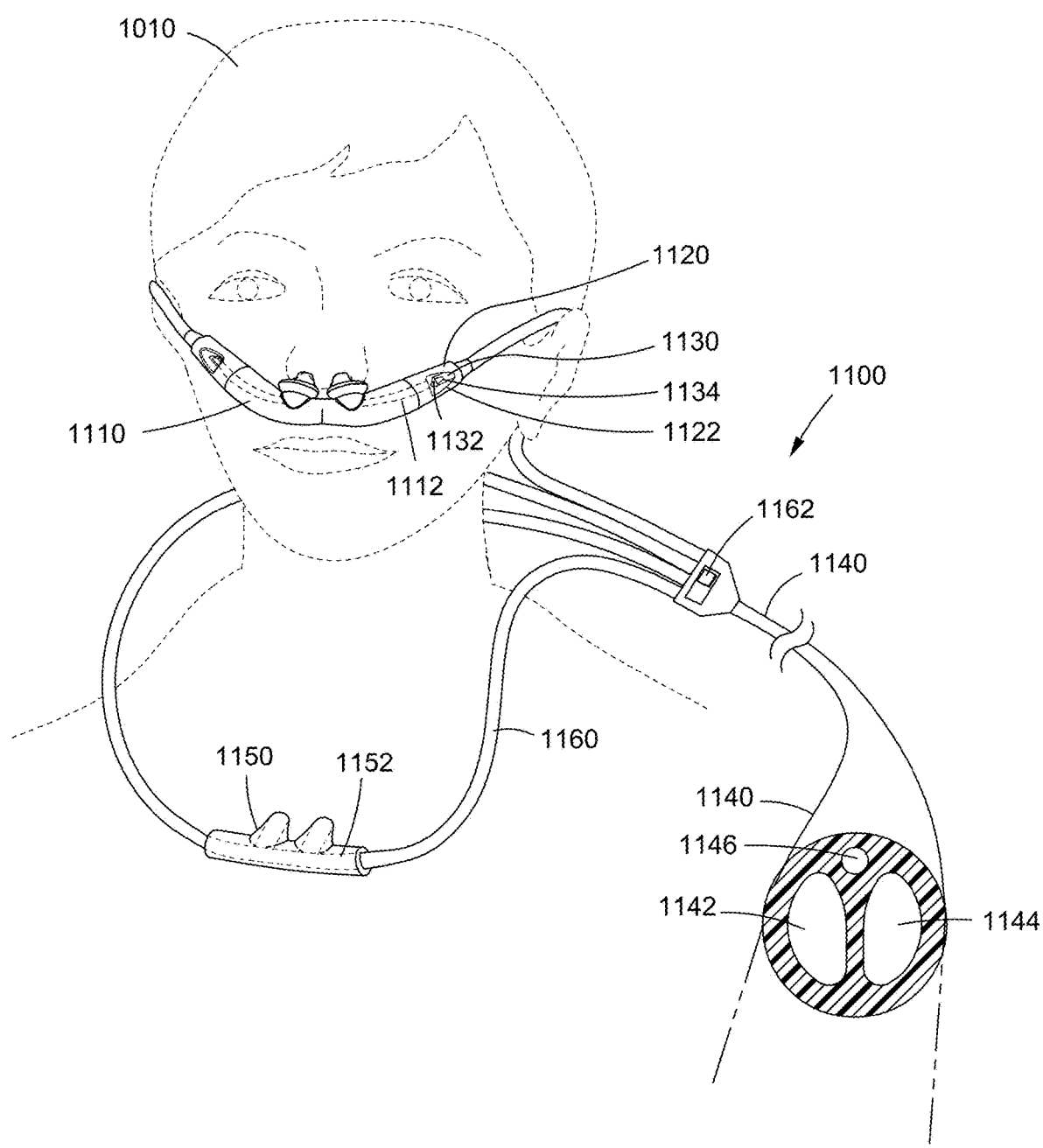
FIG. 1 shows an exemplary multifunctional ventilator interface according to an embodiment of the present disclosure.

FIG. 1 shows an exemplary multifunctional ventilator interface 1100 according to an embodiment of the present disclosure, along with a patient 1010 (or other user) who is shown receiving ventilation therefrom. In order to provide ventilation to the patient 1010, the multifunctional ventilator interface 1100 may include a manifold housing 1110 defining a ventilation gas pathway 1112. The manifold housing 1110 may be a manifold housing of a patient interface with integrated jet pump as described in Applicant's U.S. Patent Application Pub. No. 2019/0099570 and below in relation to FIGS. 4-21. In this regard, the multifunctional ventilator interface 1100 may further include a jet pump housing 1120 and a jet nozzle 1130. Ventilation gas introduced by the jet nozzle 1130 into the ventilation gas pathway 1112 may facilitate entrainment of ambient air through one or more entrainment ports 1122 defined by the jet pump housing 1120. The entrained air may mix with the ventilation gas to increase total flow to the patient 1010.

The ventilation gas may be provided from a ventilator to the jet nozzle 1130 by multi-lumen tubing 1140, such as one or more segments of tri-lumen or quad-lumen tubing defining at least a high-pressure gas lumen 1142, a low-pressure gas lumen 1144, and a pressure sensing lumen 1146. For example, ventilation gas output by the ventilator may flow through the high-pressure gas lumen 1142 and out of a high-pressure jet nozzle outlet port 1132 of the jet nozzle 1130 into the ventilation gas pathway 1112. In some cases, supplemental oxygen may also be provided, either from the ventilator or from a separate oxygen concentrator or other oxygen source that is connected to the multi-lumen tubing 1140 downstream of the ventilator. For example, a low-pressure jet nozzle outlet port 1134 of the jet nozzle 1130 may deliver oxygen from the low-pressure gas lumen 1144 to the ventilation gas pathway 1112. The pressure sensing lumen 1146 may be used as a sense line between the ventilation gas pathway 1112 and the ventilator. In order to accurately reflect patient pressure, the connection of the pressure sensing lumen 1146 to the ventilation gas pathway 1112 may typically be downstream of the jet nozzle 1130. Along these lines, it is contemplated that the manifold housing 1110 may also define a discrete pressure sensing pathway which fluidly communicates with a prescribed region of the ventilation gas pathway 1112 and is fluidly coupled to the pressure sensing lumen 1146 of the multi-lumen tubing 1140. Exemplary ventilators and oxygen concentrators that may be used with the disclosed embodiments include those described in Applicant's U.S. Pat. No. 10,369,320 issued Aug. 6, 2019, U.S. Patent Application Pub. No. 2019/0307981, published Oct. 10, 2019, U.S. patent application Ser. No. 16/862,240, filed Apr. 28, 2020 and entitled "PORTABLE OXYGEN CONCENTRATOR RETROFIT SYSTEM AND METHOD," and U.S. patent application Ser. No. 16/874,472, filed May 14, 2020 and entitled "O2 CONCNETRATOR WITH SIEVE BED BYPASS AND CONTROL METHOD THEREOF," the entire contents of each of which is expressly incorporated herein by reference.

Unlike conventional systems, the multi-functional ventilator interface 1100 is designed to accommodate convenient connection to a separate nasal cannula 1150 for delivery of continuous $O_2$ therapy instead of ventilation. In this respect, along with the nasal cannula 1150 defining a continuous $O_2$ therapy gas pathway 1152, the multi-functional ventilator interface 1100 may include an additional segment of tubing 1160 that fluidly couples the low-pressure gas lumen 1144 of the multi-lumen tubing 1140 with the continuous $O_2$ therapy gas pathway 1152 of the nasal cannula 1150. The coupling may be achieved by branching the low-pressure gas lumen 1144 using a wye connector 1160, with one branch continuing along the multi-lumen tubing 1140 to the jet nozzle 1130 and the other branch extending within the separate segment of tubing 1160 (e.g. a single-lumen tube) to the nasal cannula 1150. When the patient 1010 wishes to switch therapies from ventilation to continuous $O_2$ therapy (e.g. to take a shower or eat), the patient 1010 need not necessarily exchange one entire system for another and may simply swap the manifold housing 1110 (including the jet pump housing 1120 and jet nozzle 1130) with the nasal cannula 1150, which may be within easy reach around the patient's neck for example. The unused manifold housing 1110 may then similarly be stowed around the patient's neck until the patent 1010 is ready to switch back to ventilation.

As shown, the multi-lumen tubing 1140 may be bifurcated into two lengths of tubing, one that is associated with a left side of the manifold housing 1110 (and the patient's left nostril) and another that is associated with a right side of the manifold housing 1110 (and the patient's right nostril). For example, there may be separate left and right ventilation gas pathways 1112 within the manifold housing 1110 (though these may in some cases be fluidly connected), as well as left and right jet pump housings 1120 and left and right jet nozzles 1130. This bifurcation, which is preferably downstream of the branching off of the low-pressure gas lumen 1144, may be achieved, for example, using a wye (or "Y") connector 1160 as described in Applicant's U.S. Patent Application Pub. No. 2019/0099570 and below in relation to FIGS. 4-21 or U.S. Pat. No. 9,038,635 issued May 26, 2015, the entire contents of which is also expressly incorporated herein by reference. In some cases, the bifurcated lengths of tubing may have fewer lumens, with one length of tubing used for high-pressure gas and low-pressure gas and the other length of tubing used for high-pressure gas and the sense line, for example. Along the same lines, the tubing 1160 used for continuous $O_2$ therapy may be bifurcated into two lengths of tubing associated with left and right sides of the nasal cannula 1150.

When the patient 1010 switches to continuous $O_2$ therapy using the multifunctional ventilation interface 1100, the high-pressure gas lumen 1142 of the multi-lumen tubing 1140 may be turned off by a change in setting of the ventilator. However, since the low-pressure gas lumen 1144 will still be providing oxygen, it may be preferable to prevent the oxygen from going to the jet nozzle 1130 in order to avoid wasting oxygen. By the same token, when the patient 1010 switches back to ventilation, it may be preferable to prevent the oxygen from going to the nasal cannula 1150. To this end, it is contemplated that the wye connector 1160 used to branch the low-pressure gas lumen 1144 may include a switch 1162 for toggling between ventilation and continuous $O_2$ therapy. When continuous $O_2$ therapy is selected, the wye connector 1160 may block the branch that continues along the low-pressure gas lumen 1144 so that oxygen cannot flow farther downstream along the multi-lumen tubing 1140. When ventilation is selected, the wye connector 1160 may block the branch that enters the tubing 1160.

It is also contemplated that the multi-function ventilation interface 1100 may be configured such that the jet nozzle(s) 1130 are not outfitted with the low-pressure jet nozzle outlet port(s) 1134, and thus not adapted to introduce low pressure oxygen into the ventilation gas pathway 1112. In this instance, the multi-lumen tubing 1140 may be bifurcated (and possibly re-bifurcated downstream of the initial bifurcation) such that the high-pressure gas lumen 1142 fluidly communicates with the high-pressure jet nozzle outlet port(s) 1132 of the jet nozzle 1130 and hence the ventilation gas pathway 1112, with the pressure sensing lumen 1146 fluidly communicating with the discrete pressure sensing pathway of the manifold housing 1110 which, as indicated above, fluidly communicates with a prescribed region of the ventilation gas pathway 1112. Thus, the low-pressure gas lumen 1144 would be bifurcated from the multi-lumen tubing 1140 (and possible re-bifurcated downstream of the initial bifurcation) to fluidly communicate solely with the nasal cannula 1150. The implementation of this alternative architecture could potentially be used to simplify the protocols or eliminate the wye connector structures that may otherwise be necessary to reduce or prevent oxygen waste. In this regard, the selection of a ventilation mode on the ventilator may be used to solely facilitate high-pressure air delivery from the ventilator and the manifold 1110 and sense line communication therebetween, with the selection of an $O_2$ therapy mode being used to solely facilitate the delivery of low-pressure oxygen from the ventilator to the $O_2$ therapy gas pathway 1152 of the nasal cannula 1150.

Figure 2:
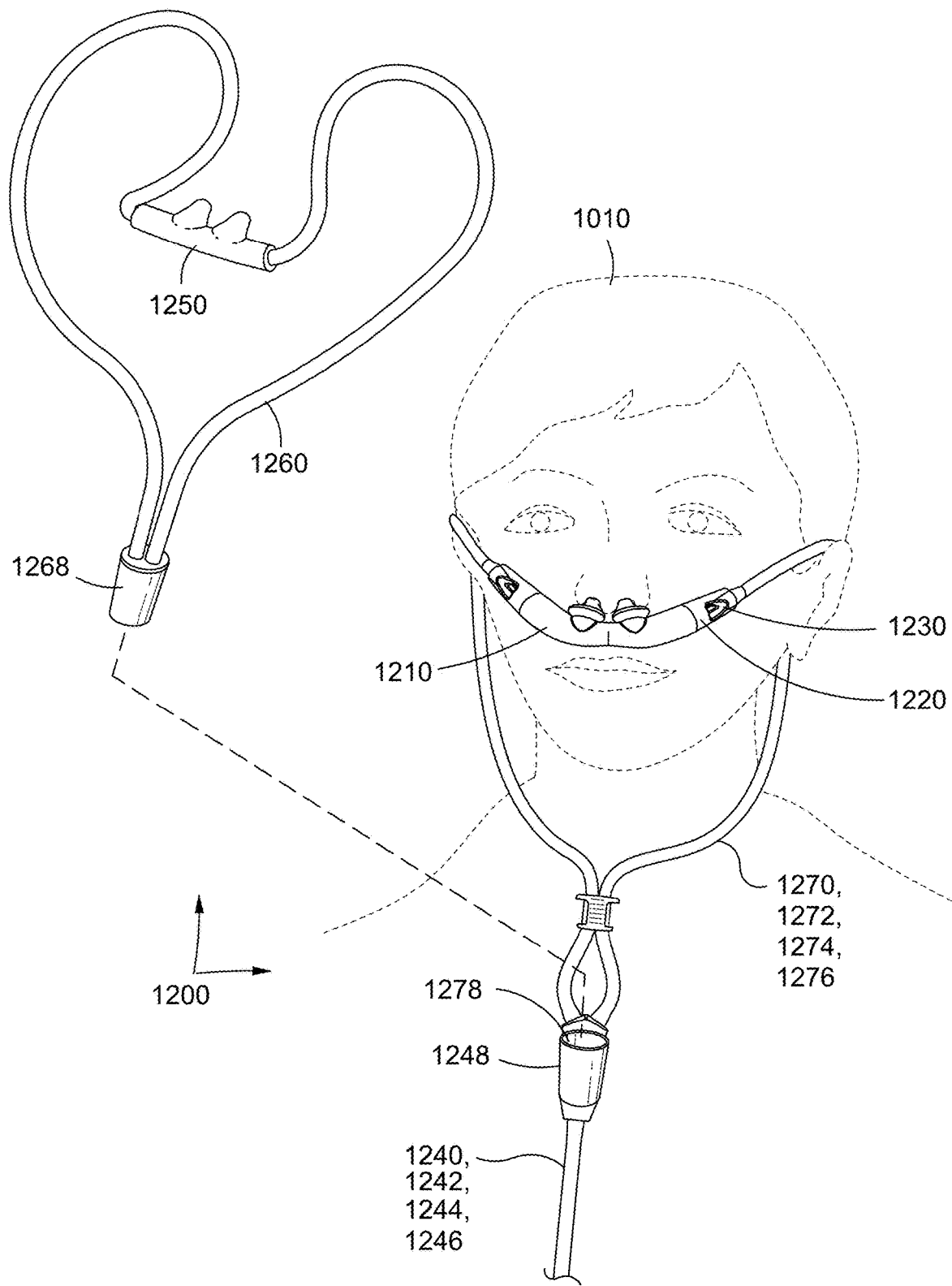
FIG. 2 shows another exemplary multifunctional ventilator interface according to an embodiment of the present disclosure.

FIG. 2 shows another exemplary multifunctional ventilator interface 1200 according to an embodiment of the present disclosure, along with a patient 1010 who is shown receiving ventilation therefrom. Like the multifunctional ventilator interface 1100 of FIG. 1, the multifunctional ventilator interface 1200 of FIG. 2 may allow the patient 1010 to conveniently switch from ventilation to continuous $O_2$ therapy by swapping a manifold housing 1210 (including a jet pump housing 1220 and jet nozzle 1230) with a nasal cannula 1250. In FIG. 2, the details of the manifold housing 1210, jet pump housing 1220, jet nozzle 1230, and nasal cannula 1250 are omitted, as they may be the same as those of the corresponding components in FIG. 1. The multifunctional ventilator interface 1200 of FIG. 2 may also include a first segment of tubing 1240 that may be the same as the multi-lumen tubing 1140 and may similarly define a high-pressure gas lumen 1242, a low-pressure gas lumen 1244, and a pressure sensing lumen 1246. However, unlike in the case of the multifunctional ventilator interface 1100, the first segment of tubing 1240 of the multifunctional ventilator interface 1200 terminates in a first quick connect fitting 1248, which may be a female coupling as shown. The manifold housing 1210, and in particular the jet nozzle 1230 thereof, may be fluidly connected to a second segment of tubing 1270 that defines a high-pressure gas lumen 1272 and terminates in a second quick connect fitting 1278 (e.g. a male coupling). When the patient is receiving ventilation as shown in FIG. 2, the first segment of tubing 1240 may be connected to the second segment of tubing 1270 by the connection of the first and second quick connect fittings 1248, 1278, such that the high-pressure gas lumen 1242 of the first segment of tubing 1240 is fluidly coupled with the high-pressure gas lumen 1272 of the second segment of tubing 1270. In this way, ventilation gas output by the ventilator may flow through the high-pressure gas lumen 1242 of the first segment of tubing 1240, through the high-pressure gas lumen 1272 of the second segment of tubing 1270, and out of a high-pressure jet nozzle outlet port of the jet nozzle 1230 into a ventilation gas pathway of the manifold housing 1210.

Along the same lines, a low-pressure gas lumen 1244 and a pressure sensing lumen 1246 of the first segment of tubing 1240 may be fluidly coupled with a low-pressure gas lumen 1274 and a pressure sensing lumen 1276 of the second segment of tubing 1270 via the quick connect fittings 1248, 1278. In a case where two lengths of tubing are to be associated with left and right sides of the manifold housing 1210 (e.g. for delivery of ventilation gas and/or supplemental oxygen to the patient's left and right nostrils), the connection of the quick connect fittings 1248, 1278 may also function to bifurcate the first segment of tubing 1240 as described above and may, for example, utilize the structure of a wye connector as described in U.S. Patent Application Pub. No. 2019/0099570 and below in relation to FIGS. 4-21.

In order to accommodate the patient's continuous $O_2$ therapy needs, the multifunctional ventilator interface 1200 may further include, in addition to the nasal cannula 1250, a third segment of tubing 1260 that terminates in a third quick connect fitting 1268 (e.g. a male coupling) and defines a low-pressure gas lumen in fluid communication with the nasal cannula 1250. When the patient 1010 wishes to switch therapies from ventilation to continuous $O_2$ therapy (e.g. to take a shower or eat), the patient 1010 may disconnect the second quick connect fitting 1278 from the first quick connect fitting 1248 and connect the third quick connect fitting 1268 in its place. The patient 1010 may then simply swap the manifold housing 1210 (including the jet pump housing 1220 and jet nozzle 1230), which is no longer fluidly coupled to the ventilator, with the nasal cannula 1250, which is now fluidly coupled to the ventilator. The unused portion of the multifunctional ventilator interface 1200 (e.g. the manifold housing 1210, jet pump housing 1220, jet nozzle 1230, and second segment of tubing 1270 during continuous $O_2$ therapy) may easily be stowed around the patient's neck or in the patient's pocket.

By using the quick connect fittings 1248, 1268, 1278 rather than branching off the low-pressure gas lumen 1144 as in the example of FIG. 1, there is no possibility that oxygen will be wasted and no need for the multifunctional ventilation interface 1200 to include a switch as described above. The quick connect fittings 1248, 1268, 1278 may simply block all unused lumens of the multi-lumen tubing 1240. For example, during continuous $O_2$ therapy, the quick connect fitting 1268 may block the high-pressure gas lumen 1242 and the pressure sensing lumen 1246 of the multi-lumen tubing 1240 while fluidly coupling the low-pressure gas lumen 1244 with the low-pressure gas lumen of the tubing 1260. During ventilation, the quick connect fitting 1278 need not block any of the lumens 1242, 1244, 1246 (assuming the ventilation therapy includes supplemental oxygen).

Figure 3A:
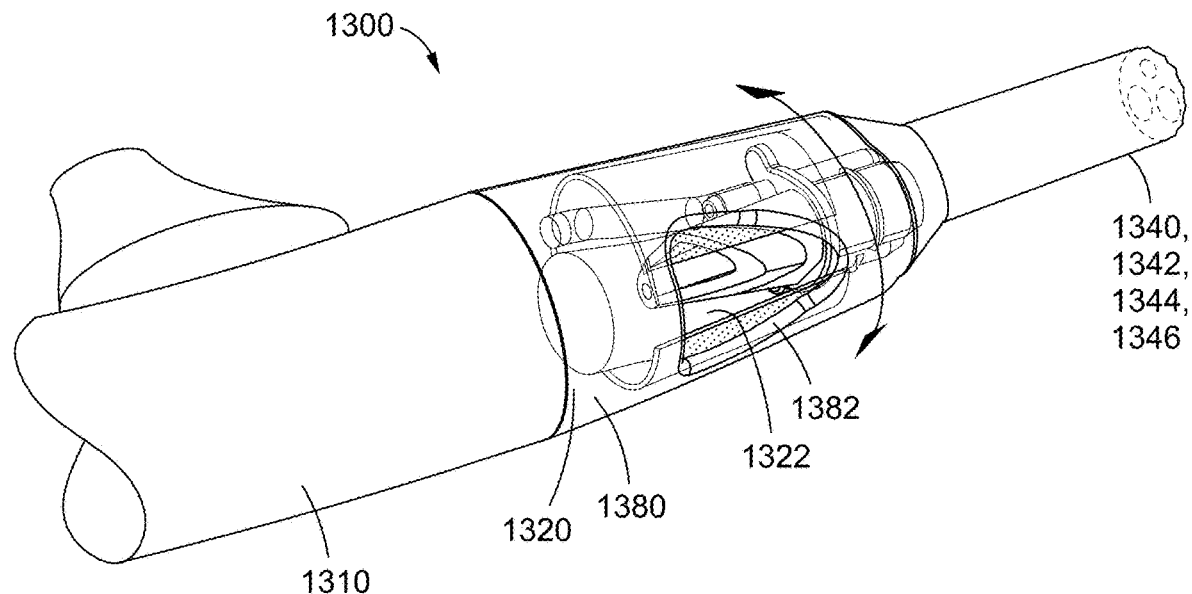
FIG. 3A shows another exemplary multifunctional ventilator interface according to an embodiment of the present disclosure.
Figure 3B:
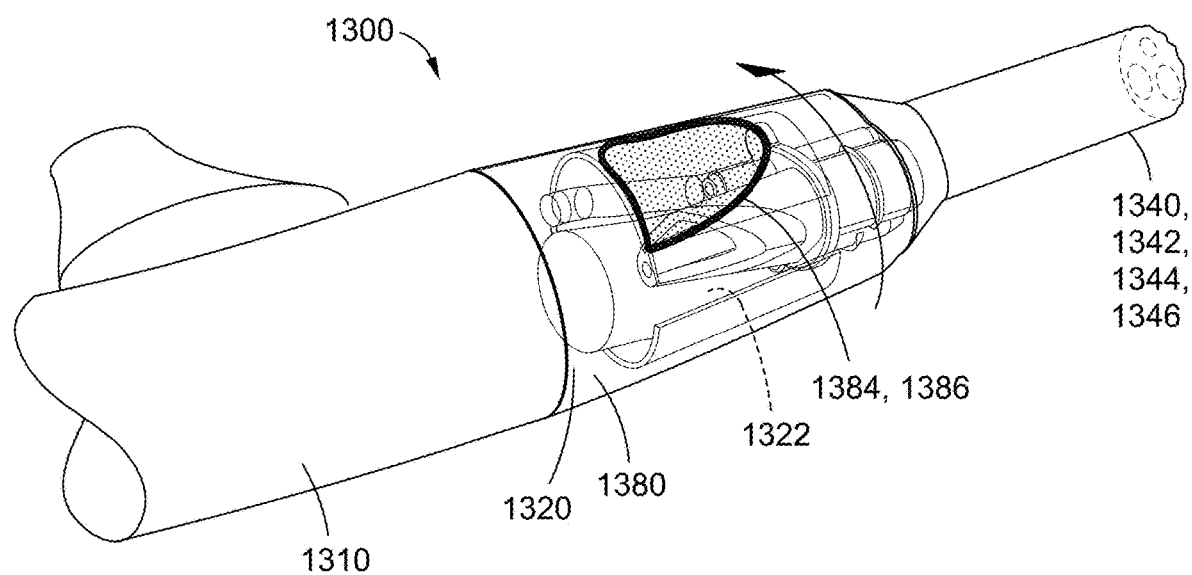
FIG. 3B shows the multifunctional ventilator interface of FIG. 3A with a rotatable sleeve thereof in a prescribed state of rotation.

FIGS. 3A and 3B show another exemplary multifunctional ventilator interface 1300 according to an embodiment of the present disclosure. Like the multifunctional ventilator interfaces 1100, 1200 of FIGS. 1 and 2, the multifunctional ventilator interface 1300 of FIGS. 3A and 3B may allow the patient 1010 to conveniently switch from ventilation to continuous $O_2$ therapy. However, the multifunctional ventilator interface 1300 provides such convenient switching in a single nasal interface that does not need to be swapped with another. In this regard, the multifunctional ventilator interface 1300 may include a manifold housing 1310, a jet pump housing 1320, and a jet nozzle that may be the same as the corresponding components in FIGS. 1 and 2 (and may be the same as the manifold assembly 104, jet pump housing 114, and jet nozzle 136 of U.S. Patent Application Pub. No. 2019/0099570 as describe below in relation to FIG. 4-21, for example) except as follows. Whereas the entrainment port 1122 shown in FIG. 1 remains open to ambient air at all times, the entrainment port 1322 of the jet pump housing 1320 may be blocked and sealed by a rotatable cap or sleeve 1380 that may be rotated about the jet pump housing 1320 as shown by the arrows in FIGS. 3A and 3B.

As shown in FIG. 3A, the sleeve 1380 may have a first window 1382 that is configured to allow ambient air to flow into the entrainment port 1322 when they are fully or at least partially in registry with each other. The first window 1382 may be sized and shaped to match the entrainment port 1322, i.e., they may have identical profiles, though there could also be variances in such profiles. In FIG. 3A, the sleeve 1380 is rotated so that the first window 1382 at least partially lines up or aligns with the entrainment port 1322, with partial alignment being used to reduce the amount of entrainment during ventilation according to the patient's prescription. As shown in FIG. 3B, the sleeve 1380 may also have a second window 1384 that is located on another part of the sleeve 1380. Like the first window 1382, the second window 1384 may be sized and shaped to match the entrainment port 1322. The second window 1384 may be on the opposite side of the sleeve 1380, for example, at a rotational position of the sleeve 1380 that is one hundred eighty degrees (180°) away from the first window 1382. In this way, the first and second windows 1382, 1384 may be selectively alignable with the entrainment port 1322 by rotation of the sleeve 1380. Unlike the first window 1382, the second window 1384 may include a one-way valve 1386 such as a flapper valve that is cooperatively engaged to the sleeve 1380 and effectively covers the second window 1384 in a manner which prevents ambient air from flowing into the entrainment port 1322 when the second window 1384 (and hence the valve 1386) is fully or at least partially aligned therewith, while still allowing the patient 1010 to exhale through the entrainment port 1322 via the second window 1384 and valve 1386.

The multifunctional ventilator interface 1300 of FIG. 3 may also include multi-lumen tubing 1340 that may be the same as the multi-lumen tubing 1140 and may similarly define a high-pressure gas lumen 1342, a low-pressure gas lumen 1344, and a pressure sensing lumen 1346, differing only in the lack of any branching to a separate nasal cannula 1150.

When the patient 1010 wishes to switch therapies from ventilation to continuous $O_2$ therapy (e.g. to take a shower or eat), the mode of the ventilator may simply be switched without any need for the patient 1010 to change nasal interfaces. The jet nozzle may then deliver oxygen from the low-pressure gas lumen 1344 of the multi-lumen tubing 1340 into the gas pathway of the manifold housing 1310. Since entrained ambient air is not needed, the patient 1010 may simply rotate the sleeve 1380 so that the first window 1382 is no longer aligned with the entrainment port 1322 and instead the second window 1384 having the one-way valve 1386 is aligned with the entrainment port 1322. In this way, the patient 1010 may effectively close the entrainment port 1322 to harmful elements in the outside environment, such as water droplets during a shower. At the same time, the one-way valve 1386 may allow the patient 1010 to continue exhaling normally through the entrainment port 1322.

Figure 3C:
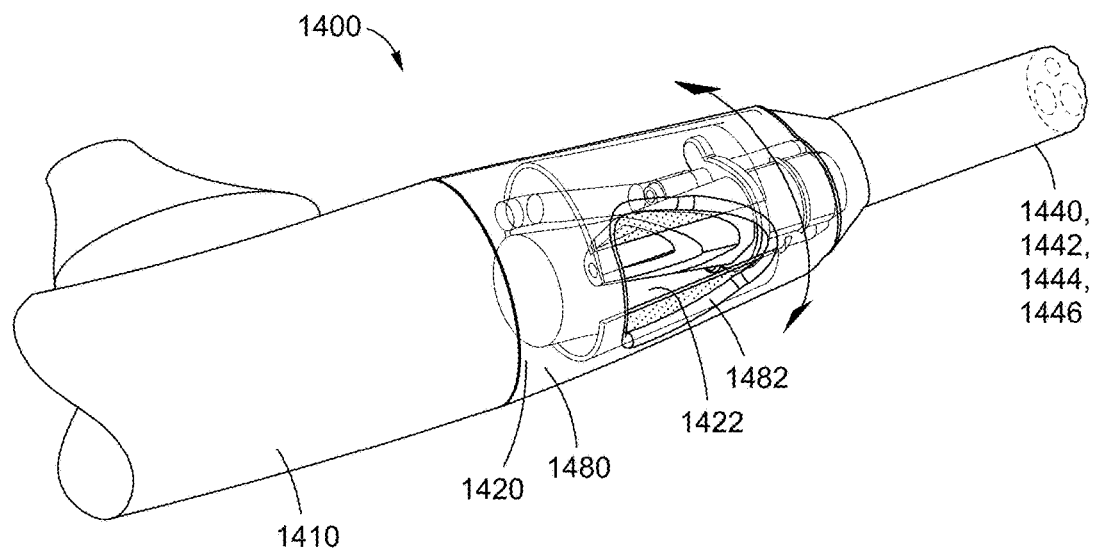
FIG. 3C shows another exemplary multifunctional ventilator interface according to an embodiment of the present disclosure.
Figure 3D:
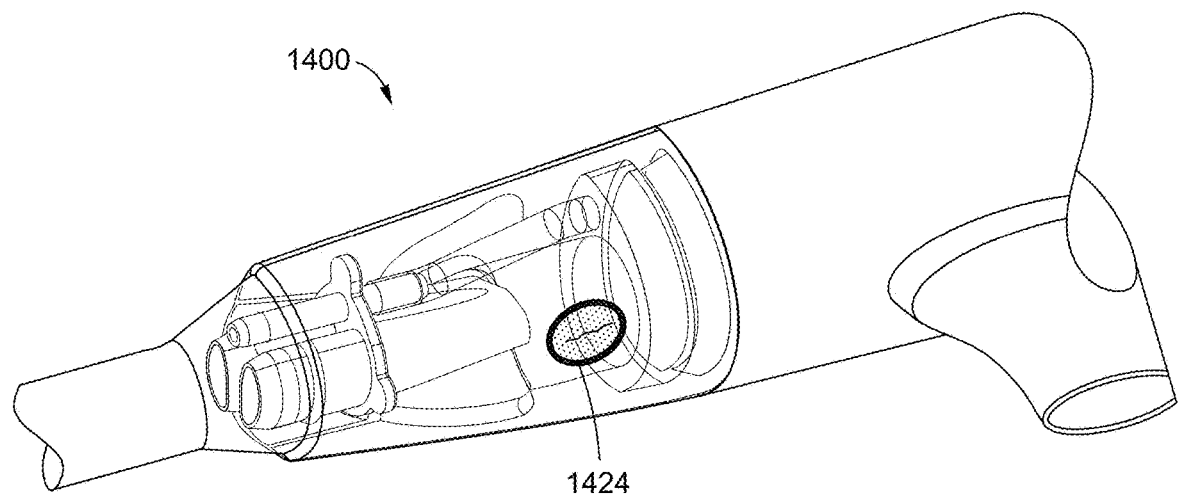
FIG. 3D shows the multifunctional ventilator interface of FIG. 3C with a rotatable sleeve thereof in a prescribed state of rotation.

In an alternative implementation of a multifunctional ventilator interface 1400, as shown in FIGS. 3C and 3D, it is contemplated that that a jet pump housing 1420 of a manifold housing 1410 may be configured to include a one-way exhaust valve 1424 integrated therein in a location which is opposite an entrainment port 1422 (i.e., separated by an interval of about 180°). In this instance, a sleeve 1480 would be outfitted with only the first window 1482. The selective rotation of the sleeve 1480 in the manner described above could be used to selectively facilitate either the full or at least partial alignment of the first window 1482 with the entrainment port 1422 (thereby allowing for ambient air flow into the jet pump housing 1420) or the full or at least partial alignment of the first window 1482 with the exhaust valve 1424 (thereby preventing ambient air from flowing into the entrainment port 1422 due to the blockage thereof while still allowing the patient 1010 to exhale via the valve 1424 and the first window 1482). As will be recognized, when the valve 1424 is effectively blocked or covered by the sleeve 1480, patient exhalation is accommodated by the simultaneously unblocked entrainment port 1422. In all other respects, the multifunctional ventilator interface 1400, manifold housing 1410, jet pump housing 1420, entrainment port 1422, sleeve 1480, and first window 1482 may be the same as the multifunctional ventilator interface 1300, manifold housing 1310, jet pump housing 1320, entrainment port 1322, sleeve 1380, and first window 1382 described above in relation to FIGS. 3A and 3B.

In either of the implementations described above, it is also contemplated that the sleeve 1380, 1480 the jet pump housing 1320, 1420 and/or the manifold housing 1310, 1410 may be outfitted with modalities (e.g., detents, stops, or other features) that prevent the sleeve 1380, 1480 from assuming any orientation wherein patient exhalation cannot flow through the at least partially unobstructed entrainment port 1322, 1422 or the at least partially unobstructed exhaust valve 1424. Moreover, those of ordinary skill in the art will recognize that in the multifunctional ventilator interface 1300, 1400 which is typically outfitted with an opposed pair of the jet pump housings 1320, 1420 (including corresponding jet nozzles and entrainment ports 1322, 1422) cooperatively engaged to the manifold housing 1310, 1410, either or both of such jet pump housings 1320, 1420 may be provided with a corresponding sleeve 1380, 1480 included as part of either of the aforementioned implementations.

In addition, irrespective of whether the sleeve 1380, 1480 is provided in either of the implementations described above, it is further contemplated that the manifold housing 1310, 1410 may include an additional one-way intake valve integrated therein. This intake valve is separate from the one-way exhaust valve(s) 1386 that is/are integrated into one or both sleeves 1380, or the exhaust valve(s) 1424 that is/are integrated into one or both jet pump housings 1420. This intake valve is preferably positioned in close proximity to the nares of the user or patient, such as at a location within the manifold housing 1310, 1410 at or proximate to the base of the nasal pillows, cushions or other structures that deliver gas to the patient's nose or nasal airways. During patient inhalation or inspiration, ambient air is able to flow though the intake valve and into the interior of the manifold housing 1310, 1410. This flow supplements that which is introduced into the interior of the manifold housing 1310, 1410 via the jet pump housing(s) 1320, 1420 and is used to satisfy a requisite patient inspiratory flow volume. While the intake valve allows flow into the interior of the manifold housing 1310, 1410 during patient inhalation, it normally blocks outflow during patient exhalation. Thus, patient exhalation is accommodated by the exhaust valves in the above-described manner.

Figure 4:
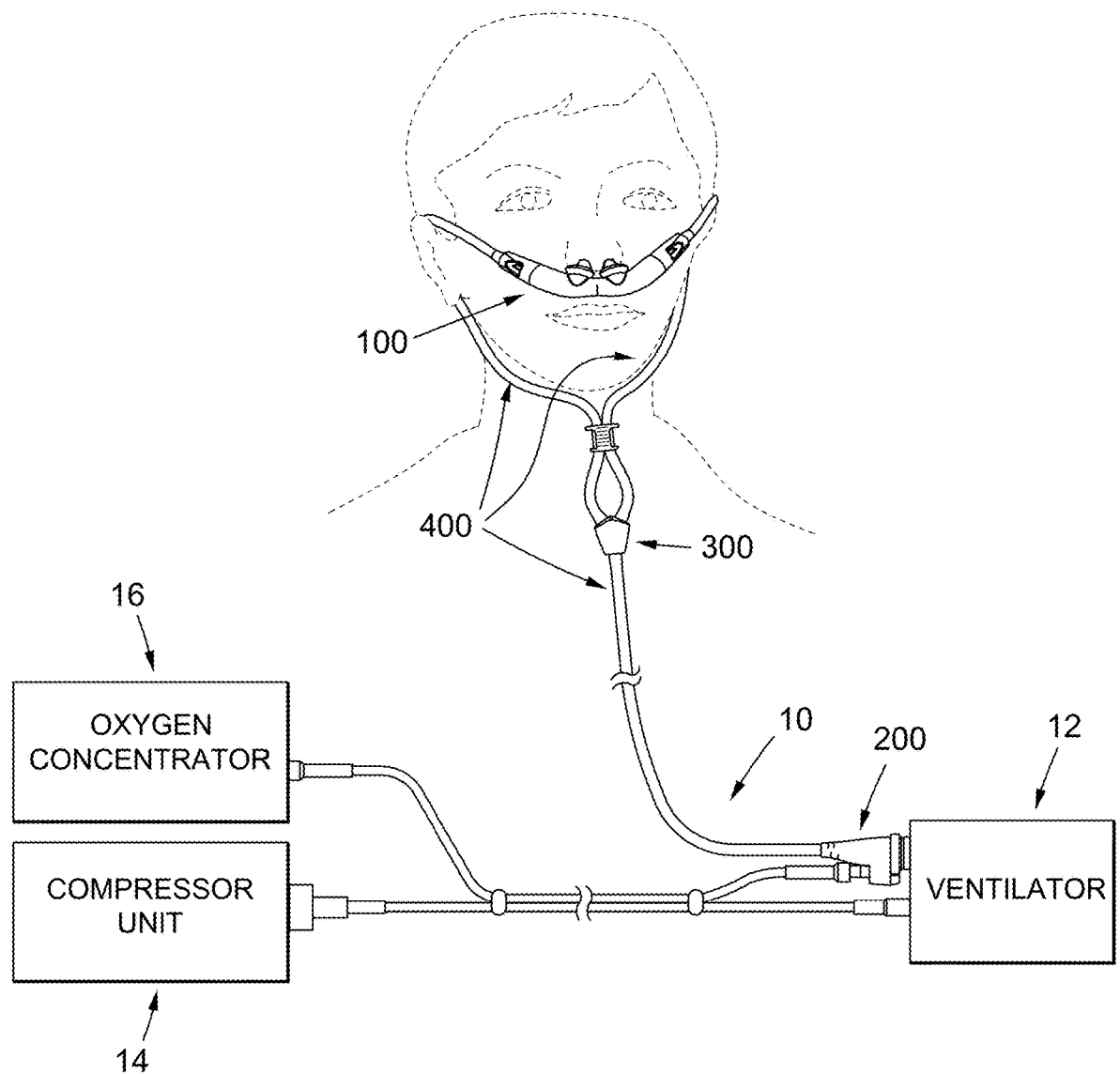
FIG. 4 is a schematic depiction of a patient circuit constructed in accordance with the present disclosure.

FIG. 4 provides a schematic representation of a patient circuit 10 constructed in accordance with the present disclosure. The patient circuit 10 is particularly suited for use in conjunction with the ventilation system described with particularity in Applicant's U.S. Patent Publication No. 2017/0209662 A1 published Jul. 27, 2017, the entire disclosure of which is incorporated herein by reference. As described in that published document, the modular ventilation system is capable of transitioning between a stationary configuration, an extended range configuration, and a stand-alone configuration, with corresponding methods of use providing continuous or intermittent ventilatory support for the care of individuals who require mechanical ventilation. Such modular ventilation system is primarily composed of a ventilator 12, a compressor unit 14, and a patient interface which, for purposes of the subject application and for consistency with the further description below, is labeled in FIG. 4 with the reference number 100.

As indicated above, the ventilation system comprising the ventilator 12, compressor unit 14, and patient circuit 10 (including the patient interface 100) may be used in at least three different configurations, including a stationary configuration, an extended range configuration, and a stand-alone configuration. In the stationary configuration, the ventilator 12 is docked with the compressor unit 14, with the patient circuit 10 (and hence the patient interface 100) being connected to the ventilator 12 (or to the ventilator 12 via the compressor unit 14) for ventilation of a stationary patient. In the extended range configuration, which may enable the patient to engage in localized daily living activities, the ventilator 12 is not docked with the compressor unit 14, but instead is near the patient, where it receives compressed air from the compressor of the compressor unit 14 via a compressed gas supply hose, with the patient circuit 10 connected to the ventilator 12. In the stand-alone configuration, which may enable the patient to engage in non-localized activities, the ventilator 12 is not docked or otherwise connected with the compressor unit 14, but instead is connected to and receives compressed gas from an external compressed gas source such as an oxygen or air cylinder, or hospital wall source, with the patient circuit 10 being connected to the ventilator 12. In either of the stationary, stand-alone or extended configurations, the patient circuit 10 may also receive low-pressure oxygen which supplements the high-pressure air delivery from an oxygen source, such as an oxygen concentrator 16.

In general terms, the patient circuit 10 comprises four (4) primary features. These are: 1) a nasal pillows style patient 100 interface that incorporates at least one "Venturi effect" jet pump proximal to the patient; 2) a three-way primary connector 200 that is configured to be placed into fluid communication with (i) a ventilator/compressor combination to facilitate the delivery of high pressure air, (ii) a ventilator/compressor combination and to an oxygen concentrator to facilitate the delivery of high pressure air in combination with supplemental low-pressure oxygen bypassing the compressor/ventilator, (iii) an oxygen a canister or wall connection via a ventilator (with the compressor being removed from the ventilation system) and further with an oxygen concentrator to allow for patient ventilation with oxygen and also with additional oxygen from the concentrator, (iv) an oxygen canister or wall connection via a ventilator (with the compressor and the oxygen concentrator being removed from the ventilation system) to facilitate the delivery of oxygen from the canister or wall connection; and (v) an oxygen canister or wall connection via the ventilator (with the compressor and the oxygen concentrator being removed from the ventilation system) and to the low pressure port of the regulator used with the canister to allow for the patient ventilation with oxygen while also receiving additional oxygen from the same gas source; 3) a three-way wye connector 300 that is fluidly connectible to the primary connector 200 and is configured to effectively bifurcate three (3) separate and distinct flow paths for high pressure air or oxygen flow, low pressure oxygen flow, and the pressure sensing, into two sets of those three paths, each such set being adapted to for placement into for effective fluid commination to respective ones of opposed end portions of the patient interface 100; and 4) tri-lumen tubing 400, which is provided in at least three (3) separate and distinct segments, one of which is used to facilitate the fluid communication between the primary connector 200 and the wye connector 300, with the remaining two segments being used to facilitate the fluid communication between the wye connector 300 and respective ones of the opposed end portions of the patient interface 100. For purposed of clarity, the structural and functional features of the patent interface 100, primary connector 200, wye connector 300 and tri-lumen tubing 400 will be broken down into separate sections bellows.

The Tri-Lumen Tubing

Figures 5, 6:
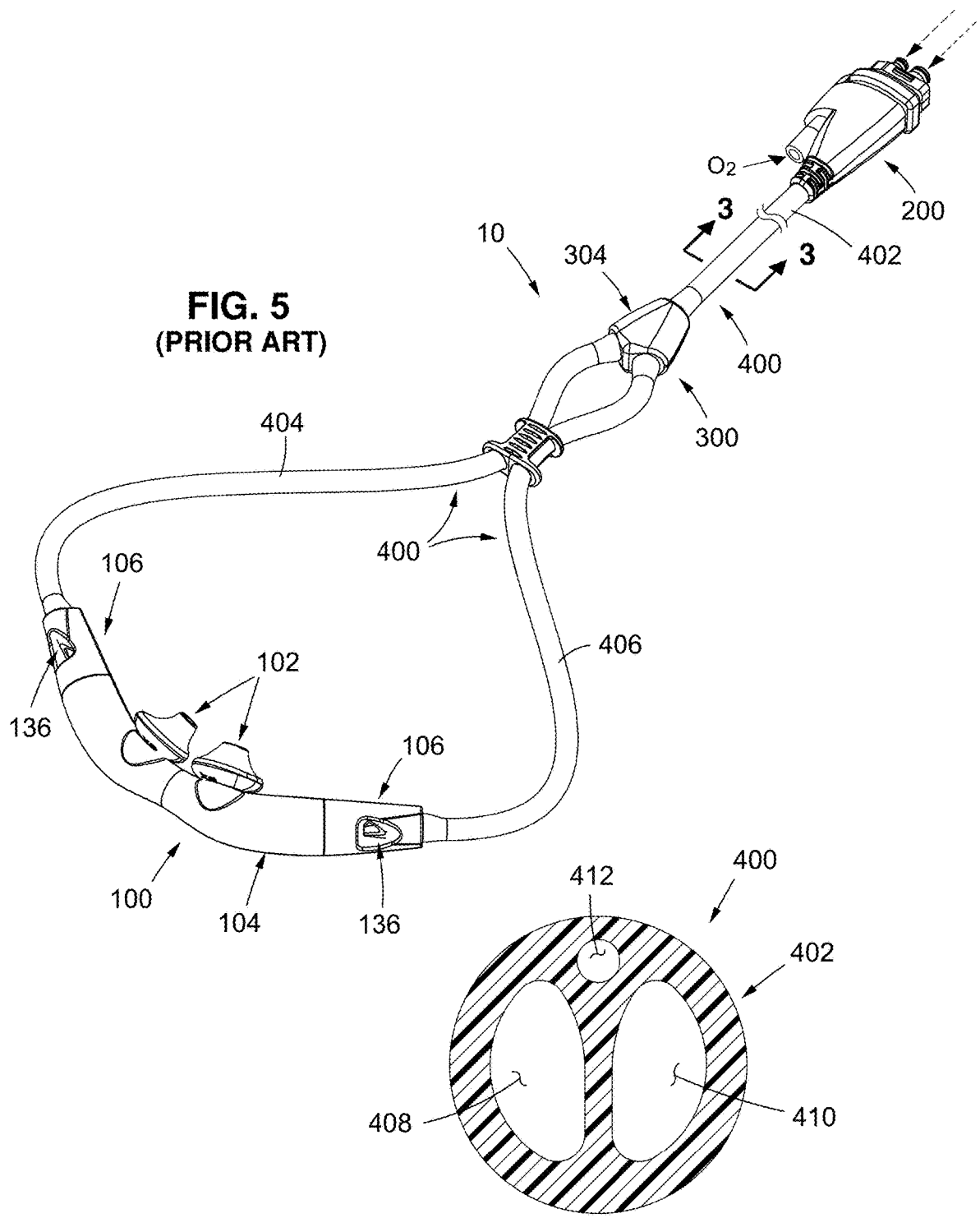
FIG. 5 is a top perspective view of the patient circuit constructed in accordance with the present disclosure.
FIG. 6 is a cross-sectional view of one of the three segments of tri-lumen tubing included in the patient circuit, taken along line 3-3 of FIG. 5.

FIG. 5 provides a schematic representation of the patient circuit wherein three (3) separate segments of the tri-lumen tubing 400 are used to facilitate the fluid communication between the primary connector 200 and the wye connector 300, and between the wye connector 300 and respective ones of the opposed end portions of the patient interface 100. These include a first segment 402 extending between the primary connector 200 and the wye connector 300, a second segment 404 extending between the wye connector 300 and one opposed end portion of the patient interface 100, and a third segment 406 extending between the wye connector 300 and the remaining opposed end portion of the patient interface 100.

With reference to FIG. 6, the three lumens defined by each segment 402, 404, 406 the tri-lumen tubing 400 include an air/oxygen (or high-pressure gas) delivery lumen 408, a low-pressure oxygen (or gas) delivery lumen 410, and a pressure sensing lumen 412. The tubing 400 is approximately 5.5 mm in diameter and, within the patient circuit 10, the second and third segments 404, 406 may be routed around the ears of the patient in the manner shown in FIG. 7. As will be described in more detail below, the high-pressure air/oxygen (or gas) delivery lumen 408 is for high pressure air emanating from the combination of the ventilator 12 and compressor unit 14 or for oxygen (or another gas) emanating from the ventilator 12 alone, with the low-pressure oxygen (or gas) delivery lumen 410 being for supplemental oxygen emanating from an oxygen concentrator, and the pressure sensing lumen 412 being used as a sense line between the ventilator 12 and the patient interface 100, all of these lumens 408, 410, 412 being fluidly isolated from each other.

The Patient Interface

Turning now to FIG. 8, a perspective view of an exemplary embodiment of an assembled patient interface 100 is illustrated, showing a nasal connector assembly 102, a manifold assembly 104, and a pair of jet pump assemblies 106.

In the patient interface 100, the nasal connector assembly 102 includes one or more nasal connectors 108. As used herein, the term "nasal connector(s)" may include nasal pillows or cushions, barbs, sleeves, cannulas, and other devices that deliver gas from a gas source to a patient's nose or nasal airways. For illustrative purposes only, the figures illustrate nasal pillows; however, it is understood that any reference to a nasal pillow could similarly refer to any type of nasal connector 108. The one or more nasal connectors 108 of the nasal connector assembly 102 may be directly attached to the manifold assembly 104, may fixed at a distance from the manifold assembly 104, or may be detached from the manifold assembly 104.

In the exemplary embodiment, the nasal connectors 108 used in the nasal connector assembly 102 are nasal pillows, which may impinge on a rim of the nostril, seal on the rim of the nostril, seal inside the nostril, impinge on the tissue underneath the nose, or interface with the nostril according to combinations of the above. Nasal pillows may typically be soft and compliant to allow for comfortable contact with the nostril and, if a seal is intended, compress against the nostril in a comfortable manner. Nasal pillows may typically include convolutions in the shape to allow the extension to flex in multiple planes, and to compresses along a centerline axis, to conform to the user's nose. Nasal pillows may seal against the nostril rim or other part of the nostril so that there is not inadvertent leakage between the nasal pillows and nose and so that the majority of the breathing gas flows through the nasal pillows. However, this seal does not need to be leak free, and in some embodiments, there may be a desired gas flow between the nasal pillows and the nostril. Nasal pillows may be available in different sizes so that the user can select a size that matches their anatomy. It may also be seen that these variations are equally applicable to any form of nasal connector 108 of a nasal connector assembly 102, and as such, other forms of nasal connector 108 besides nasal pillows may be customized or optimized according to the needs or desires of the user or the specific attributes of the patient interface 100.

The manifold assembly 104 may be formed of rigid, semi-rigid, or flexible/elastic materials, or may be formed of a combination of such materials, which may include a manifold assembly 104 formed having sections varying in their rigidity and softness. The external components of the manifold assembly 104, in the exemplary embodiment, together form a multi-part assembly that may include a front piece 110 and a rear piece 112 that snap together around the internal components of the manifold assembly. The manifold 104, when assembled, may have an external compound arcuate shape that is most advantageous to mate with the facial anatomy. Alternatively, the external shape manifold assembly 104 may be substantially straight, or be shaped in other configurations.

Each jet pump assembly 106 may include a jet pump housing 114 having defined therein one or more entrainment ports 116 open to ambient air. In the exemplary embodiment, each jet pump assembly 106 has a jet pump housing 114 configured with one entrainment port 116. However, it is contemplated that in other embodiments, two or more entrainment ports per jet pump assembly 106 may be utilized, such as, for example, to reduce risk of a blockage during side sleeping by a user. If a first entrainment port is blocked by the user's position during sleep, a second entrainment port may still be exposed to ambient air and may allow for proper ventilation treatment of the user. It is also contemplated that each entrainment port 116 need not constitute a single aperture, but may constitute, for example, a plurality of apertures, so long as its purpose of permitting ambient air to be entrained therethrough is accomplished.

Turning now to FIG. 9, an exploded view of the components of a patient interface 100 is illustrated, showing the internal components of the manifold assembly 104 and the internal components of the jet pump assembly 106.

As may be seen, the manifold assembly 104 may further comprise an inner tube assembly 118. The inner tube assembly 118 may be formed of a rigid, semi-rigid, malleable, or flexible material, such as, for example, silicone rubber or other similar materials, which may allow for molding of complex shapes that are not manufactural in mass with harder materials. The inner tube assembly 118 may be defined by one or more main gas flow tube portions 120, and in the exemplary embodiment, is defined by left and right gas flow tube portions 120. Each gas flow tube portion 120 defines a gas flow pathway 122 for delivering ventilation gas from the corresponding jet pump assembly 106, through the manifold assembly 104, and to the nasal connector assembly 102 wherein it may be provided to the patient. Each gas flow pathway 122 may refer to a path for gas through the inner tube assembly 118, either as one single pathway, such as from a jet pump assembly 106 to a nasal connector 108, or as multiple pathways. Each gas flow pathway 122 typically includes a flow path that is generously radiused to offer and low resistance to flow.

The inner tube assembly 118 may, in the exemplary embodiment, have the compound arcuate curve of the exterior of the manifold assembly 104. In other embodiments, however, the inner tube assembly 118 may be shaped in other ways, such as curving in other directions, such as inferiorly, or may be straight, or may be substantially malleable so as to adopt the configuration to which the remainder of the manifold assembly 104 is adjusted to. The inner tube assembly 118 may also be integral to the manifold.

The inner tube assembly 118 may be further defined by, as shown in the exemplary embodiment, one or more interconnector portions 124 between the one or more gas flow tube portions 120 defining an interconnector gas flow path 126 which places the gas flow pathways 122 defined by the gas flow tube portions 120 into fluid communication with each other. The interconnector portion 124 may function to balance pressure between the left and right nasal airways or to shut flow to the least resistive nostril. This may provide additional safety for the user in the case that one nostril is blocked. The interconnector portion 124 may also provide for a smaller and more symmetrical device.

The gas flow tube portions 120 and/or the interconnector portion 124 of the inner tube assembly 118 may include, on its outer surface, bumps or protrusions 128, which may be used to create a space between the inner tube assembly 118 and the inner walls of the external components of the manifold assembly 104, such as the front piece 110 and the rear piece 112 of the exemplary multi-piece snap-together embodiment of the manifold assembly 104. The bumps or protrusion 128, serving as spacers between the inner tube assembly 118 and the manifold assembly 104, may help promote the function of draining fluids which may accumulate between the inner tube assembly 118 and the manifold assembly 104. Such fluid may drain from the space between the inner tube assembly 118 and the inner walls of the external components of the manifold assembly 104, such as the front piece 110 and the rear piece 112 of the exemplary multi-piece snap-together embodiment of the manifold assembly 104, being removed from the manifold assembly 104 via weep holes 130 in the external components of the manifold assembly 104. In the exemplary embodiment, the weep holes 130 are positioned on the lower side of the manifold assembly 104, so as to drain downward when conventionally worn, and are formed at the junction of the snapped-together front piece 110 and the rear piece 112.

The gas flow tube portions 120 may each be configured with one or more sensing ports 132 for connection with the distal end of one or more corresponding sensing manifold tubes 134. In the exemplary embodiment, a sensing port 132 is positioned at the distal end of each gas flow tube portion 120 so as to permit fluid access to the distal end of the corresponding main gas flow pathway 122 through the sensing port 132. However, it may be seen that in other embodiments, sensing ports 132 may be positioned at other locations of the inner tube assembly 118, or at multiple locations.

Each jet pump assembly 106 may include the aforementioned jet pump housing 114 and a jet nozzle 136 for positioning inside the jet pump housing 114. Each jet pump assembly 106 may be removably or non-removably connected to a respective one of the opposed sides of the manifold assembly 104 via, for example, but without limitation, a rotational locking connection, an interference locking connection, and/or a keyed locking connection. In the exemplary embodiment illustrated in FIGS. 9 and 10, the distal ends of the front piece 110 and the rear piece 112 contain annular detents which permit the rotational attachment of the jet pump housings 114 to the manifold assembly 104. It will be recognized that through the use of a removable connection of the manifold assembly 104 to the jet pump housings 114, the manifold assembly 104 may be partially disassembled and removed from the jet pump assemblies 106, such as through the disconnection of the front piece 110 from the rear piece 112. Along these lines, it may be beneficial for the method of connecting the jet pump assemblies 106 to the manifold assembly 104 to permit rotation and/or other repositioning of the jet pump assemblies 106 relative to the manifold assembly 104.

Turning now to FIG. 10, a front view of an exemplary embodiment of the internal components of an assembled patient interface 100 is shown. Each jet nozzle 136, in the exemplary embodiment, has a proximal, upstream end and a distal, downstream end, with at least three fluidly isolated lumens therethrough. Each lumen has an opening at each of the proximal and distal ends of the jet nozzle 136. At the proximal end of each jet nozzle 136 is a high-pressure jet nozzle inlet port 138, a low-pressure jet nozzle inlet port 140, and a sensing jet nozzle inlet port 142. At the distal end of the jet nozzle 136 is a high-pressure jet nozzle outlet port 144, a low-pressure jet nozzle outlet port 146, and a sensing jet nozzle outlet port 148. The high-pressure jet nozzle outlet port 144 and the low-pressure jet nozzle outlet port 146 are configured to output into the corresponding jet pump housing 114, with the high-pressure jet nozzle outlet port 144 and the low-pressure jet nozzle outlet port 146 both being either upstream from or at least partially aligned with the entrainment port 116. As a result, the output of the respective gases from the high-pressure jet nozzle outlet port 144 and the low-pressure jet nozzle outlet port 146 achieves an entrainment effect whereby ambient air is drawn into the corresponding entrainment port 116. The outputted gases and the entrained ambient air then travels together into the corresponding gas flow pathway 122 of the manifold assembly 104 and to the nasal connector assembly 102, where it is subsequently output to the patient.

In the exemplary embodiment, the sensing jet nozzle outlet port 148 of each jet nozzle 136 is fluidly connected to a corresponding sensing manifold tube 134. Such manifold tube 134 is advanced through a corresponding lumen 135 formed within the jet pump housing 114 and extending from the sensing jet nozzle outlet port 148 toward the distal end of the corresponding jet pump housing 114. As such, the lumen 135 and corresponding sensing manifold tube 134 advanced therethrough are fluidly isolated from the gases outputted from the high-pressure jet nozzle outlet port 144 and the low-pressure jet nozzle outlet port 146, and any air entrained by those gases via the entrainment port 116. The sensing manifold tube 134 travels into the manifold assembly 104, and may be generally aligned with but fluidly isolated from the corresponding gas flow pathway 122, before connecting to the sensing port 132. In the exemplary embodiment, the sensing manifold tube 134 is fully contained within the jet pump housing 114 of the corresponding jet pump assembly 106 and the manifold assembly 104, traveling outside the gas flow tube portion 120 but within the front piece 110 and rear piece 112. However, it may be seen that in other embodiments, the sensing jet nozzle outlet port 148 and the sensing tube 134 may be configured differently, such as embodiments where the sensing tube 134 travels within the corresponding gas flow pathway 122, and as such may not require the presence of a sensing port 132, but may instead sense at wherever the distal end of the sensing tube 134 is positioned.

Figure 11:
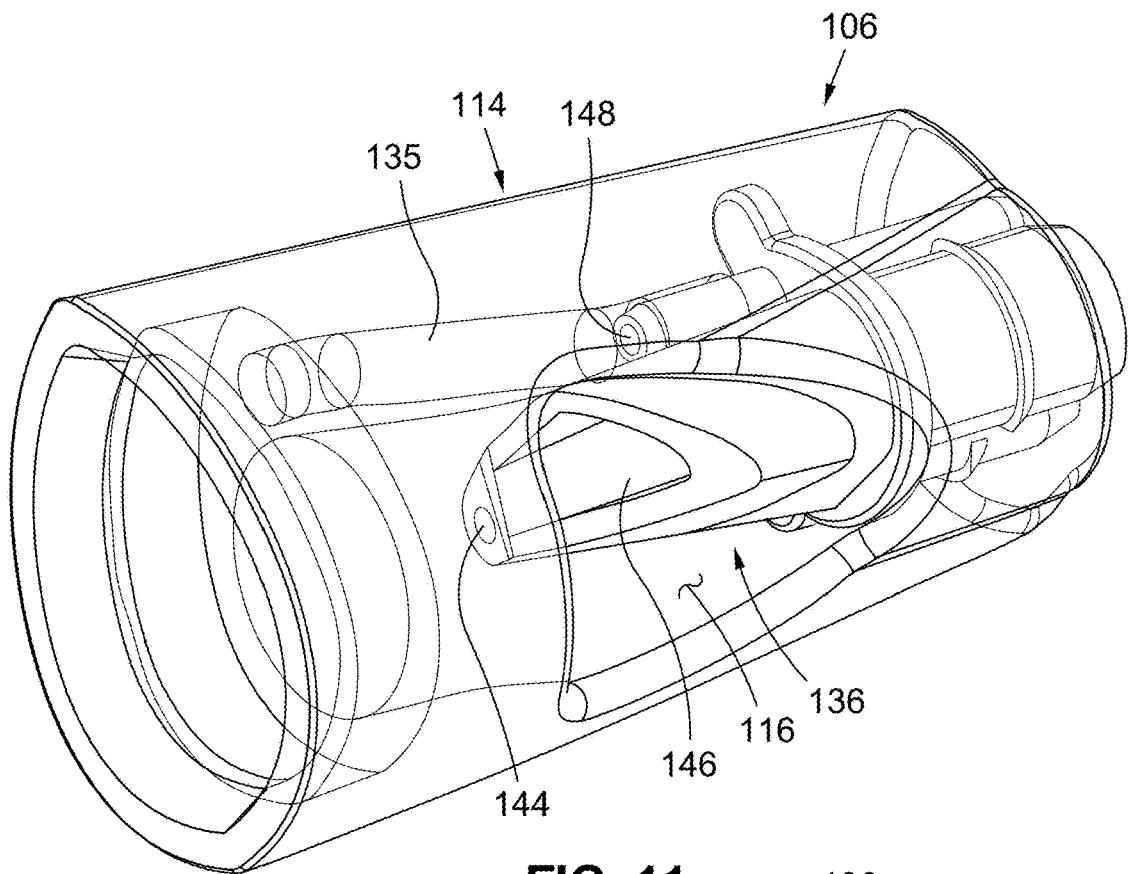
FIG. 11 is an output side perspective view of one of the two jet pump assemblies integrated into the patient interface, the housing of the assembly being shown as transparent to more clearly depict other features of the assembly.

Turning now to FIG. 11, an x-ray proximal perspective view of the internal components of a jet pump assembly 106 according to the exemplary embodiment is illustrated. In the exemplary embodiment, a substantial portion of the distal end of the jet nozzle 136 may be configured to be substantially oblique to the axial direction of the lumens passing therethrough. The low-pressure jet nozzle outlet port 146 is disposed in closer proximity to the entrainment port 116 and more rearward, while the high-pressure jet nozzle outlet port 144 is disposed at the most distal point of the jet nozzle assembly 136, further from the entrainment port 116 and forward from the low-pressure jet nozzle outlet port 146. In the exemplary embodiment, the low-pressure jet nozzle outlet port 146 is approximately crescent shaped about the lumen terminating in the high-pressure jet nozzle outlet port 144.

The aforementioned arrangement of the high and low pressure jet nozzle outlets 144, 146 relative to the entrainment port 116 may result in entrainment of ambient air in a fashion that maximizes laminar flow and minimizes turbulence of gases in the corresponding gas flow pathway 122 due to the interposition of the lower pressure gas between the high pressure gas and the entrained air serving as at least a partial buffer for shielding the high-pressure gas from the entrained air, resulting in the creation of a smoother shear force gradient across the gas flow cross section than would result without such interposition. When the gases from all three of the sources eventually blend together, they do so in a fashion that results in a more laminar fluid flow. More laminar flow of gas delivered to a patient is associated with improved user comfort and decreased noise. As may be seen, without such a shielding effect, the direct exposure of the maximum shear forces of the gas from the high-pressure jet nozzle outlet port 144 to the ambient air that is entrained through the entrainment port 116 would be more prone to generate turbulent eddy, resulting in stronger turbulence and reduced laminar flow, which is associated with reduced user comfort. Furthermore, the relatively small diameter of the high-pressure jet nozzle outlet port 144 relative to the size of the low-pressure jet nozzle outlet port 146 acts to reduce the surface area of the high-pressure gas output from the high-pressure jet nozzle outlet port 144, further reducing the likelihood of developing regions of extreme shear force disparity that lead to turbulent flow. Thus, each of the above-described Venturi-effect jet pump assemblies 106 converts and multiply high pressure/low flow breathable gas delivered by the ventilator into high flow/low pressure gas for the patient. As indicated above, the low-pressure jet nozzle outlet port 146 associated with each of the jet pump assemblies 106 is designed in a way that the positive pressure created during the delivery of the highest acceptable oxygen flow (i.e., 5 l/min) is not more than 0.5 cmH2O. As a result, and as also indicated above, such low-pressure jet nozzle outlet port 146 is effectively designed to be a very inefficient jet pump so that any delivered flow will not interfere with the proper operation of the corresponding high-pressure jet nozzle outlet port 144. This is achieved by keeping a large cross-sectional area of the low-pressure jet nozzle outlet port 146, thus having a very low flow velocity and virtually no entrainment potential.

Figure 12:
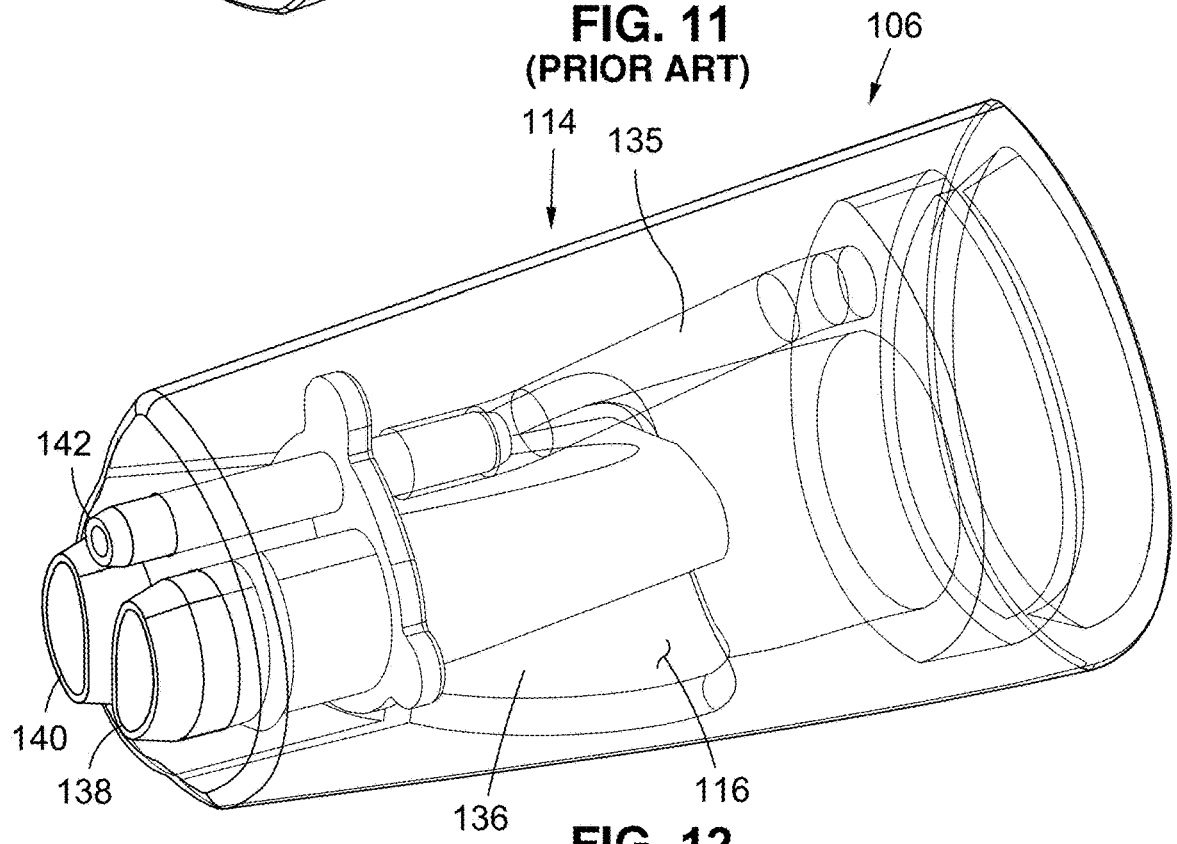
FIG. 12 is an input side perspective view of one of the two jet pump assemblies integrated into the patient housing, the housing of the assembly being shown as transparent to more clearly depict other features of the assembly.
Figure 13:
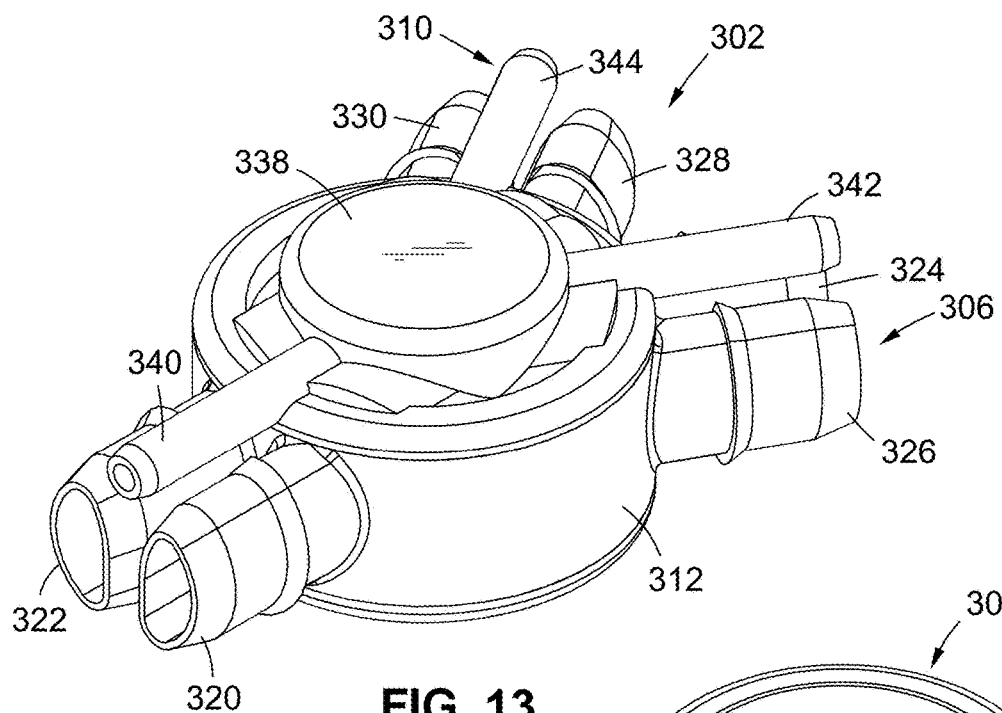
FIG. 13 is a top perspective view of the wye connector of the patient circuit.

Turning now to FIG. 12, an x-ray proximal perspective view of the internal components of a jet pump assembly 106 according to the exemplary embodiment is illustrated. The arrangement according to the exemplary embodiment of the high-pressure jet nozzle inlet port 138, the low-pressure jet nozzle inlet port 140, and the sensing jet nozzle inlet port 142 is more prominently illustrated. In the exemplary embodiment, the three inlets are male-type inlets designed to interface with a corresponding interface having three corresponding female-type ports. However, it may be seen that other arrangements of inlets or combinations of arrangements of inlet types may be appropriate, and may result in different advantages and disadvantages. It may also be seen how these jet nozzle inlets may interfaceable with a variety of connective lines by insertion of a multi-lumen line to the jet pump assembly 106 within or around the jet pump housing 114, or connection of one or more gas lines to the one or more inlets, including lines or multi-lumen lines which may not necessarily contain three of a low pressure gas, a high pressure gas, and a sensing line, so long as the corresponding portion of the jet nozzle 136 is occluded or otherwise not interfaced with. However, in an exemplary implementation of the patient circuit 10, it is contemplated that each jet pump assembly 106 will be cooperatively engaged to a corresponding one of the second and third segments 404, 406 of tri-lumen tubing 400 in manner wherein the high-pressure jet nozzle inlet port 138 is advanced into and frictionally retained with the corresponding high-pressure air/oxygen (or gas) delivery lumen 408, the low-pressure jet nozzle inlet port 140 is advanced into and frictionally retained with the corresponding low-pressure oxygen (or gas) delivery lumen 410, and the sensing jet nozzle inlet port 142 is advanced and frictionally maintained within the corresponding pressure sensing lumen 412. Glue (e.g., a UV glue) can also be used to facilitate such retention, as may barbs formed on the various ports and/or the retention force exerted by the corresponding, pre-molded jet pump housing 114.

The Primary Connector

One of the features of the patient circuit 10 is the three-way primary connector 200 that fluidly couples the patient interface 100 to the ventilator 12 and/or the compressor 14 (via the ventilator 12), and the oxygen concentrator 16 as described above. Referring now to FIGS. 17-19, additional details of the primary connector 200 will now be described. The primary connector 200 includes several constituent components, including a ventilator connector 202, an oxygen connector 204, and a housing 206. The ventilator connector 202 and the oxygen connector 204 includes various inlets and outlets that are configured to interface with corresponding ports of the ventilator 12 and the oxygen concentrator 16, and the tri-lumen tubing 400.

The ventilator connector 202 has a high-pressure conduit 208 with a high-pressure inlet port 208a and a high-pressure outlet port 208b. Additionally, there is a sense conduit 210 with a sense inlet port 210a and a sense outlet port 210b. The high-pressure conduit 208 and the sense conduit 210 are either mounted to or integral with a ventilator connector body 214. The size of the high-pressure inlet port 208a and the sense outlet port 210b, along with spatial relation between the same, are understood to correspond to those outlets of the ventilator 12 (or on the compressor unit 14 if the ventilator 12 is docked thereto). As shown, the passageway axis of the high-pressure conduit 208 and the passageway axis of the sense conduit 210 are laterally offset and parallel to each other. Along these lines, the cross-sectional shape of both the high-pressure inlet port 208a and the sense outlet port 210b are depicted as circular, though this is by way of example only and is understood to match the configuration of the outlets of the ventilator 12 or compressor unit 14.

In order to maintain a fluidly sealed connection to the ventilator 12, the high-pressure inlet port 208a and the sense outlet port 210b may each incorporate o-ring gaskets 212. The high-pressure conduit 208 and the sense conduit 210 may be fabricated from a rigid or semi-rigid material, such that the malleable or flexible materials in the corresponding interface on the ventilator 12, as well as the tri-lumen tubing 400 can be fitted thereon while maintaining a sealed relationship.

Both the high-pressure conduit 208 and the sense conduit 210 narrow at the high-pressure outlet port 208b and the sense inlet port 210a, respectively, to match the size, shape, and spatial relation between the two to correspond to those of the high-pressure gas delivery lumen 408 and the pressure sensing lumen 412 of the tubing 400, and in particular the first segment 402 thereof. The high-pressure inlet port 208a and the high-pressure outlet port 208b are understood to be coaxial, that is, the high-pressure conduit 208 has a straight body and passageway without bends. However, the sense inlet port 210a is axially offset from that of the sense outlet port 210b, reflecting the relative positional offsets between the corresponding port of the ventilator 12 and the tri-lumen tubing 400. In this regard, the sense conduit 210 defines a bend or angularly offset segment 216 that connects the sense inlet port 210a and the sense outlet port 210b. The cross-sectional shape of the high-pressure outlet port 208b generally corresponds to that of the high-pressure gas delivery lumen 408, e.g., oval-shaped. Along the same lines, the cross-sectional shape of the sense inlet port 210a likewise corresponds to that of the pressure sensing lumen 412.

The primary connector 200, and in particular the high-pressure conduit 208 thereof, is contemplated to interconnect the ventilator 12 or compressor unit 14 to facilitate the delivery of high pressure air to the patient. As indicated above, in accordance with various embodiments, the compressor unit 14 may be connected to the docked ventilator 12 via a separate conduit, and the paths are combined into for introduction into the high-pressure conduit 208 of the ventilator connector 202 via corresponding outlets of the compressor unit 14. The delivery of additional oxygen is also contemplated through a low-pressure line that is separately connected to an oxygen supply, which may be an oxygen concentrator, an oxygen canister or wall connection to an oxygen gas source. In this regard, potential safety issues associated with pressurization of oxygen in a compressor, as well as flow sensor calibration with the combined delivery of oxygen and air may be avoided.

As briefly noted above, the primary connector 200 includes the oxygen connector 204 through which supplemental oxygen may be delivered to the patient interface 100. The oxygen connector 204 is generally defined by u-shaped low-pressure conduit 218, with a low-pressure inlet port 218a on one end and a low-pressure outlet port 218b on an opposed end. In an exemplary configuration, the opening of the low-pressure inlet port 218a faces in the opposite direction as the opening of the high-pressure inlet port 208a and the sense inlet port 210a, so that a connection to an external oxygen source may be made. There is a first bend 220, which is illustrated as perpendicular corner. There is lateral extension 222, followed by another perpendicular second bend 224 that leads to the low-pressure outlet port 218b. According to some implementations, the lateral extension 222 is open, and so there may be a plug 223 that cover such open segment.

Like the high-pressure outlet port 208b, the low-pressure outlet port 218b is sized and configured to interface with the corresponding lumen of the tri-lumen tubing 400, e.g., the low-pressure gas delivery lumen 410. As such, the low-pressure outlet port 218b is understood to have an oval cross section. Again, the tri-lumen tubing 400 is understood to be constructed of a semi-rigid or flexible material that forms a sealing relationship with the low-pressure outlet port 218b. As a further means to ensure this sealing relationship, the low-pressure outlet port 218b includes a barb 213.

The oxygen connector 204, and specifically the dimensions of the lateral extension 222, is understood to be configured for low pressure outlet port 218b to be positioned in prescribed offset relationships to the high-pressure outlet port 208b and the sense inlet port 210a. These offset relationships are understood to correspond to those of the low pressure gas delivery lumen 410 to the high pressure gas delivery lumen 408 and the pressure sensing lumen 412, such that the tri-lumen tubing 400 is attached to the ventilator connector 202 and the oxygen connector 204, with each of the conduits thereof being in fluid communication with the respective lumens of the tri-lumen tubing 400, e.g., the high pressure gas delivery lumen 408, the pressure sensing lumen 412 and the low pressure gas delivery lumen 410. The ventilator connector 202 is understood to be mounted to the oxygen connector 204, and thus there may be a support platform 226 as well as a support strut 228 for positioning the ventilator connector 202 relative to the oxygen connector 204. The pseudo-hexagonal feature on the platform 226 may be used as a plug to close the sense line.

The ventilator connector 202 and the oxygen connector 204 are disposed within the housing 206. The housing 206 thus defines a first opening 230a from which the high-pressure inlet port 208a extends, and a second opening 230b from which the sense outlet port 210b extends. According to various embodiments, the housing 206 may be fabricated from a semi-rigid or malleable material that flexibly retains the ventilator connector 202 and the oxygen connector 204 within. To minimize lateral movement of the ventilator connector 202 during insertion and removal, and to provide a keyed plug that allows for visual and tactile insertion into the corresponding socket of the ventilator 12, there may also be a connector clip 232. As shown, the connector clip 232 is defined by a square end 234 and an opposed tapered end 236. The connector clip 232 may include support frame 238 that retains the ventilator connector body 214.

The housing 206 is further defined by a tubing receiver extension 240. The tri-lumen tubing 400 is received by the housing 206, and specifically via the tubing receiver extension 240 that is opposite the openings 230 for the connection to the ventilator 12 or compressor unit 14. More particularly, the tubing receiver extension 240 includes an integral flexible grommet 242 that is contemplated to relieve the stresses imparted to the connection between the tri-lumen tubing 400, on one end, and the ventilator connector 202 and the oxygen connector 204, on the other.

The Wye Connector

The wye connector 300 comprises two main components, i.e., an interior housing 302 and an over-molded exterior housing 304. The interior housing 302 resides within the exterior housing 304, the primary purpose of which is to provide a more streamlined, aesthetically pleasing form factor for the wye connector 300.

The interior housing 302 comprises a main body 306, a low-pressure plug plate 308 attached to one side of the main body 306, and a sensing plate 310 also attached to the main body 306 in opposed relation to the plug plate 308. The main body 306 comprises an annular, circularly configured outer wall 312. While the outer wall 312 defines an opposed pair of distal rims, it does not define a continuous path or opening between such distal rims. Rather, the main body 306 also includes a separator wall 314 which spans or extends completely diametrically across the interior area defined by the outer wall 312, thus effectively segregating such interior area into a first, top section 316 and a second, bottom section 318 as viewed from the perspective shown in FIGS. 15 and 16. As will be described in more detail below, when the plug and sensing plates 308, 310 are each attached to the main body 306, and in particular to respective ones of the opposed rims defined by the outer wall 312 thereof, the plug plate 308 effectively encloses the bottom section 318. This enclosed bottom section 318 collectively defined by the outer wall 312, separator wall 314 and plug plate 308 defines a low-pressure chamber of the wye connector 300. Similarly, the sensing plate 310 effectively encloses the top section 316, with this enclosed top section 316 collectively defined by the outer wall 312, separator wall 314 and sensing plate 310 defining a sensing chamber of the wye connector 300.

Protruding from the exterior surface of the outer wall 312 of the main body 306 is a high-pressure inlet port 320 and a low-pressure inlet port 322 which are disposed in side-by-side relation to each other, and each have a generally kidney bean shaped cross-sectional profile. Also protruding from the exterior surface of the outer wall 312 of the main body 306 is a first high-pressure outlet port 324 and a first low-pressure outlet port 326 which are disposed in side-by-side relation to each other, and identically configured to the high and low-pressure inlet ports 120, 122. Further protruding from the exterior surface of the outer wall 312 of the main body 306 is a second high-pressure outlet port 328 and a second low-pressure outlet port 330 which are also disposed in side-by-side relation to each other, and identically configured to the high and low-pressure inlet ports 320, 322. When viewed from the perspective shown in FIG. 14, the arrangement of the various high and low-pressure ports is such that if the high and low-pressure inlet ports 320, 322 are viewed as being in the 6 o'clock position on the main body 306, the first high and low-pressure outlet ports 324, 326 are in the 11 o'clock position, with the second high and low-pressure outlet ports 324, 326 being in the 1 o'clock position.

Figure 14:
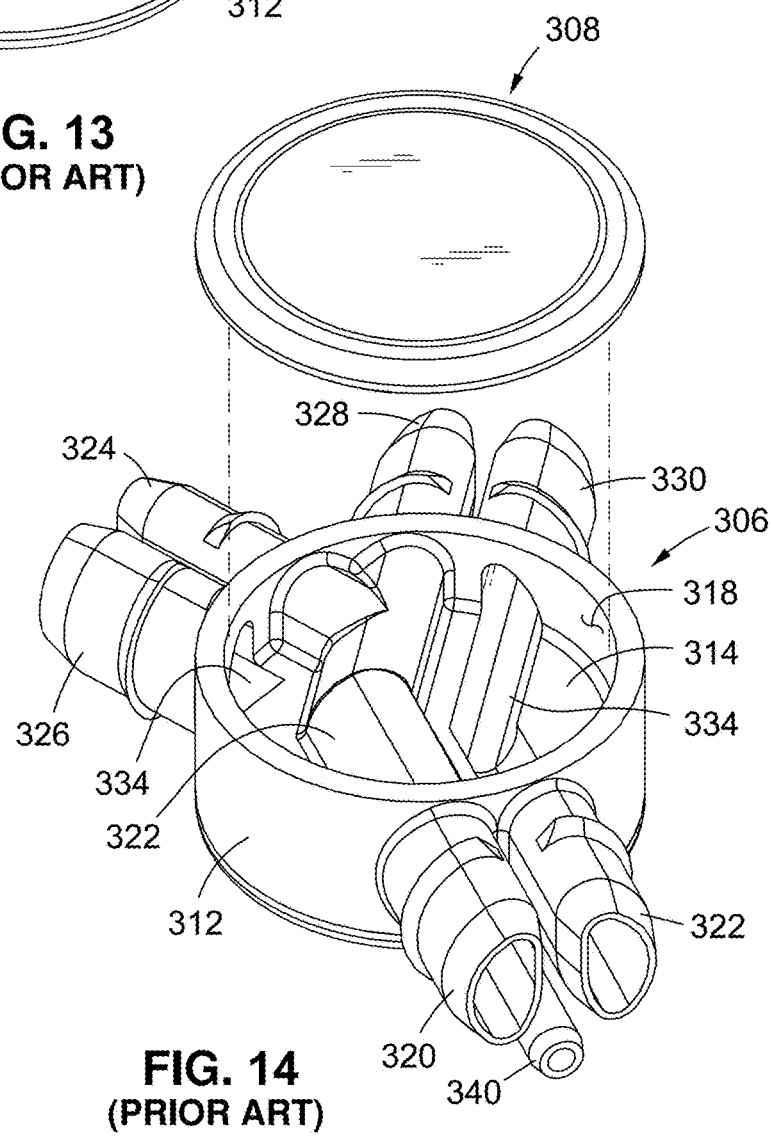
FIG. 14 is a bottom exploded view of the wye connector shown in FIG. 13 taken from a first perspective.
Figure 15:
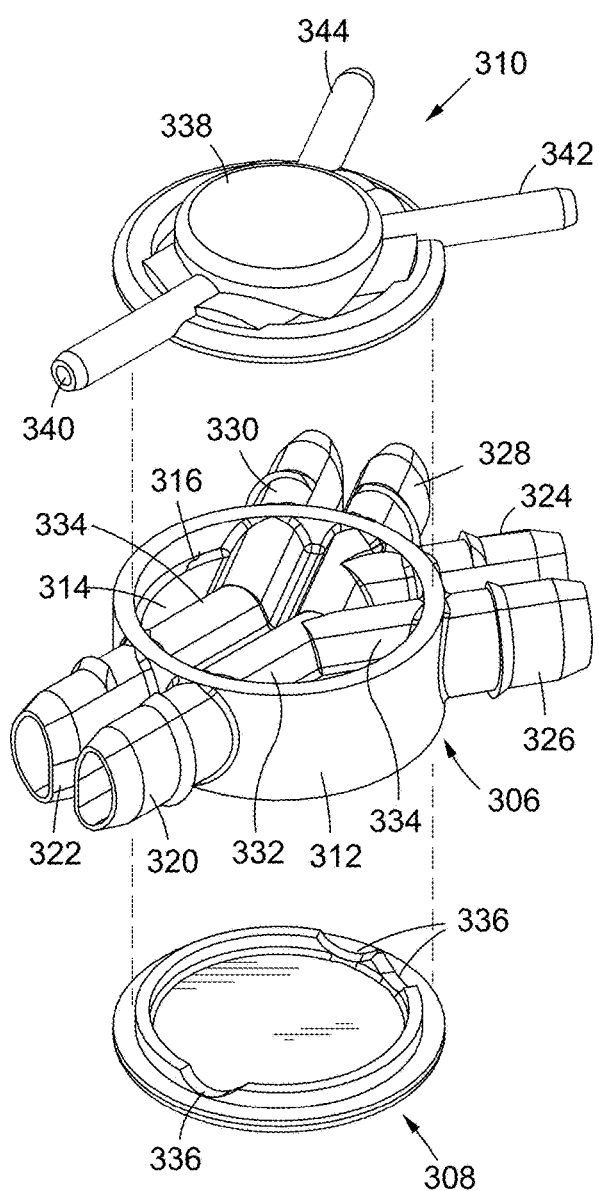
FIG. 15 is a top exploded view of the wye connector shown in FIG. 13.
Figure 16:
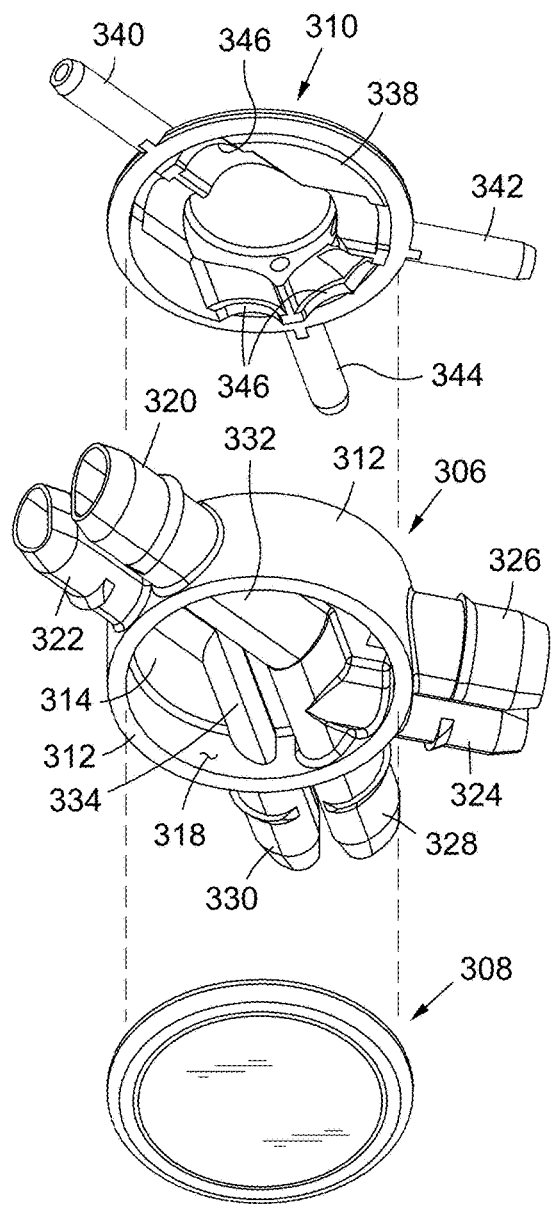
FIG. 16 is bottom exploded view of the wye connector shown in FIG. 13 taken from a second perspective.

As seen in FIGS. 14-16, the main body 306 is configured such that the high-pressure inlet port 320 is in direct fluid communication with each of the first and second high pressure outlet ports 324, 328. Such fluid communication is facilitated by an enclosed, tunnel like channel 332 which is an integral portion of the separator wall 314, with portions of the channel 332 thus protruding into each of the low-pressure and sensing chambers, though being fluidly isolated therefrom. As seen in FIGS. 14-16, a portion of the channel 332 has a generally Y-shaped configuration as allows it to effectively bifurcate flow from the high-pressure inlet port 320 into each of the first and second high-pressure outlet ports 324, 328.

As seen in FIGS. 14 and 16, the main body 306 is also configured such that the low-pressure inlet port 322 is in direct fluid communication with low-pressure chamber defined by the enclosed bottom section 318. In a similar fashion, each of the first and second low-pressure outlet ports 326, 330 is also in direct fluid communication with low-pressure chamber defined by the enclosed bottom section 318. As such, low-pressure gas entering the low-pressure chamber via the low-pressure inlet port 322 is effectively routed into each of the first and second low-pressure outlet ports 326, 330, but is fluidly isolated from the channel 332 and hence the first and second high-pressure outlet ports 324, 328. To assist is promoting flow into the low-pressure chamber from the low-pressure inlet port 322 and from the low-pressure chamber into each of the first and second low-pressure outlet ports 326, 330, it is contemplated that the underside of the separator wall 314 partially defining the low-pressure chamber may be formed to include integral grooves 334 which each have a generally semi-circular cross-sectional profile, and thus protrude into the sensing chamber, though being fluidly isolated therefrom. The grooves 334 are sized and shaped to provide an effective increase in the cross-sectional area of open communication between each of the low-pressure ports 322, 326, 330 and the low-pressure chamber.

As indicated above, in the wye connector 300, the attachment of the plug plate 308 to the corresponding rim of the main body 306 effectively encloses the bottom section 118, thus facilitating the formation of the low-pressure chamber. Along these lines, as seen in FIG. 15, the plug plate 308 is formed to include three (3) semi-circular recesses 336 about its periphery. When the plug plate 308 is attached to the main body 306, these recesses 336 are positioned to accommodate corresponding portions of the bifurcated channel 332 protruding into the low-pressure chamber.

As also indicated above, in the wye connector 300, the attachment of the sensing plate 310 to the corresponding rim of the main body 306 effectively encloses the top section 316, thus facilitating the formation of the sensing chamber. The sensing plate 310 includes a circularly configured body 338. Protruding from the body 338 is a sensing inlet port 340 which has a generally circular cross-sectional profile. Also protruding from the body 340 is a first sensing outlet port 342 and a second sensing outlet port 344 which are each identically configured to the sensing inlet port 340. When viewed from the perspective shown in FIG. 15, the arrangement of the various sensing ports is such that if the sensing inlet port 340 is viewed as being in the 6 o'clock position on the body 338, the first sensing outlet port 342 is in the 1 o'clock position, with the second sensing outlet port 344 being in the 11 o'clock position. The wye connector 300 is configured such that the sensing inlet and outlet ports 340, 342, 344 are each in direct fluid communication with sensing chamber defined by the enclosed top section 316, yet are fluidly isolated from the channel 332 (and hence the high-pressure inlet and outlet ports 320, 324, 328) as well as the low-pressure chamber (and hence the low-pressure inlet and outlet ports 322, 326, 330). As such, open fluid communication between the sensing inlet and outlet ports 340, 342, 344 is facilitated by the intervening sensing chamber. As seen in FIG. 16, the body 338 of the sensing plate 310 is formed to include six (6) semi-circular recesses 346 about its periphery. When the sensing plate 310 is attached to the main body 306, these recesses 346 are positioned to accommodate corresponding portions of the bifurcated channel 332 and grooves 334 protruding into the sensing chamber.

In an exemplary implementation of the patient circuit 10, it is contemplated that the wye connector 300 will be cooperatively engaged to each of the first, second and third segments 402, 404, 406 of tri-lumen tubing 400. In greater detail, the high and low-pressure inlet ports 320, 322 and the sensing inlet port 340 are advanced into and frictionally retained with corresponding ones of the high-pressure air/oxygen (or gas) delivery lumen 408, the low-pressure oxygen (or gas) delivery lumen 410, and the pressure sensing lumen 412 of the first tubing segment 402. Similarly, the first high and low-pressure outlet ports 324, 326 and the first sensing outlet port 342 are advanced into and frictionally retained with corresponding ones of the high-pressure air/oxygen (or gas) delivery lumen 408, the low-pressure oxygen (or gas) delivery lumen 410, and the pressure sensing lumen 412 of the second tubing segment 404, with the second high and low-pressure outlet ports 328, 330 and the second sensing outlet port 344 being advanced into and frictionally retained with corresponding ones of the high-pressure air/oxygen (or gas) delivery lumen 408, the low-pressure oxygen (or gas) delivery lumen 410, and the pressure sensing lumen 412 of the third tubing segment 406.

Patient Circuit Modes of Use

As indicated above, the patient circuit 10 of the present disclosure is capable of accommodating multiple configurations of the ventilation system. In a first of these configurations, the patient interface 100 (and hence the patient wearing the same) is placed into fluid communication with high-pressure air emanating from the ventilator 12 directly or from the ventilator 12 via the compressor unit 14 (if the ventilator 12 is docked in the compressor unit). In this arrangement, the primary connector 200 is connected to the ventilator 12 or compressor unit 14 such that high-pressure air is provided to the patient in a flow path comprising, in sequence, the high-pressure conduit 208 of the ventilator connector 202, the high-pressure air/oxygen (or gas) delivery lumen 408 of the first tubing segment 402, the channel 332 of the wye connector 300, the high-pressure air/oxygen (or gas) delivery lumens 408 of the second and third tubing segments 404, 406, and the high-pressure gas delivery lumens defining the above-described high-pressure jet nozzle inlet and outlet ports 138, 144 in the jet nozzles 136 of the jet pump assemblies 106. In this arrangement, an unobstructed pressure sensing path is also defined between the ventilator 12 and the patient interface 100 by, in sequence, the sense conduit 210 of the ventilator connector 202, the pressure sensing lumen 412 of the first tubing segment 402, the sensing inlet port 340 and the first and second sensing outlet ports 342, 344 of the wye connector 300, the pressure sensing lumens 412 of the second and third tubing segments 404, 406, the sensing lumens defining the above-described sensing jet nozzle inlet and outlets 142, 148 in the jet nozzles 136 of the jet pump assemblies 106, the sensing manifold tubes 134, and the sensing ports 132.

In a second of these configurations, the patient interface 100 is placed into fluid communication with high-pressure air emanating from the ventilator 12 directly or from the ventilator 12 via the compressor unit 14 (if the ventilator 12 is docked in the compressor unit), but also with supplemental low-pressure oxygen supplied from the oxygen concentrator 16 and bypassing the compressor unit 14 and ventilator 12. The high-pressure air delivery sequence is the same as described above for the first configuration. Oxygen from the oxygen concentrator 16 is provided to the patient in a flow path comprising, in sequence, the oxygen connector 204 of the primary connector 200, the low-pressure oxygen (or gas) delivery lumen 410 of the first tubing segment 402, the low-pressure inlet and outlet ports 322, 326, 330 of the wye connector 300, the low-pressure air/oxygen (or gas) delivery lumens 410 of the second and third tubing segments 404, 406, and the low-pressure gas delivery lumens defining the above-described low-pressure jet nozzle inlet and outlet ports 140, 146 in the jet nozzles 136 of the jet pump assemblies 106. In this arrangement, an unobstructed pressure sensing path is also defined between the ventilator 12 and the patient interface 100 in the same sequence as described above for the first configuration.

In a third of these configurations, the patient interface 100 is placed into fluid communication with oxygen emanating from a canister or wall connection via the ventilator 12 (with the compressor unit 14 being removed from the ventilation system) and further with oxygen emanating from an oxygen concentrator 16, the patient being ventilated with oxygen and also receiving additional oxygen from the concentrator 16. In this arrangement, the primary connector 200 is connected to the ventilator 12 such that oxygen from the canister or wall connection is provided to the patient in a flow path comprising, in sequence, the high-pressure conduit 208 of the ventilator connector 202, the high-pressure air/oxygen (or gas) delivery lumen 408 of the first tubing segment 402, the channel 332 of the wye connector 300, the high-pressure air/oxygen (or gas) delivery lumens 408 of the second and third tubing segments 404, 406, and the high-pressure gas delivery lumens defining the above-described high-pressure jet nozzle inlet and outlet ports 138, 144 in the jet nozzles 136 of the jet pump assemblies 106. Oxygen from the oxygen concentrator 16 is provided to the patient in a flow path comprising the same sequence as described above for the second configuration. An unobstructed pressure sensing path is also defined between the ventilator 12 and the patient interface 100 in the same sequence as described above for the first configuration.

In a fourth of these configurations, the patient interface 100 is placed into fluid communication with oxygen emanating from a canister or wall connection via the ventilator 12 (with the compressor unit 14 and the oxygen concentrator 16 being removed from the ventilation system). In this arrangement, the primary connector 200 is connected to the ventilator 12 such that oxygen from the canister or wall connection is provided to the patient in a flow path comprising, in sequence, the high-pressure conduit 208 of the ventilator connector 202, the high-pressure air/oxygen (or gas) delivery lumen 408 of the first tubing segment 402, the channel 332 of the wye connector 300, the high-pressure air/oxygen (or gas) delivery lumens 408 of the second and third tubing segments 404, 406, and the high-pressure gas delivery lumens defining the above-described high-pressure jet nozzle inlet and outlet ports 138, 144 in the jet nozzles 136 of the jet pump assemblies 106. An unobstructed pressure sensing path is also defined between the ventilator 12 and the patient interface 100 in the same sequence as described above for the first configuration.

In a fifth of these configurations, the patient interface 100 is placed into fluid communication with oxygen emanating from a canister or wall connection via the ventilator 12 (with the compressor unit 14 and the oxygen concentrator 16 being removed from the ventilation system), with the low-pressure oxygen port of the primary connector 200 of the patient circuit 10 being connected to the low pressure port of the regulator used with the canister to allow the patient to be ventilated with oxygen while also receiving additional oxygen from the same gas source, i.e., the canister. In this arrangement, oxygen from the canister or wall connection is provided to the patient in a flow path comprising the same sequence as described above for the fourth configuration. Additional oxygen from the same source is provided to the patient in a flow path comprising, in sequence, the oxygen connector 204 of the primary connector 200, the low-pressure oxygen (or gas) delivery lumen 410 of the first tubing segment 402, the low-pressure inlet and outlet ports 322, 326, 330 of the wye connector 300, the low-pressure air/oxygen (or gas) delivery lumens 410 of the second and third tubing segments 404, 406, and the low-pressure gas delivery lumens defining the above-described low-pressure jet nozzle inlet and outlet ports 140, 146 in the jet nozzles 136 of the jet pump assemblies 106. In this arrangement, an unobstructed pressure sensing path is also defined between the ventilator 12 and the patient interface 100 in the same sequence as described above for the first configuration.

Alternative Arrangements

As indicated above, and with reference to FIGS. 20 and 21, in one possible alternative embodiment, the patient circuit 10a is provided with an oxygen connector 600, compatible with 6 mm oxygen cannula connectors, that can be glued or clipped over the wye connector 300a of the patient circuit 10a. The wye connector 300a differs from the wye connector 300 through the elimination of the above-described low-pressure inlet and outlet ports 322, 326, 330. In a similar vein, in the patient circuit 10a, the primary connector 200a differs from the primary connector 200 through the elimination of the above-described oxygen connector 204, with a first segment 402a of bi-lumen tubing 400a replacing the first segment 402 of tri-lumen tubing 400, as only two lumens are needed to effectuate high pressure gas delivery and pressure sensing fluid communication between the primary connector 200a and wye connector 300a in the patient circuit 10a.

From the oxygen connector 600, a single tube 602 can deliver oxygen to one or a pair of delivery nozzles that can be glued or clipped in place over or around one entrainment area or respective ones of the entrainment areas of the jet pump assembles 106a included in the patient interface 10a. In other words, the tube 602 (e.g., oxygen line) may deliver gas to one delivery nozzle, and be extended to deliver the gas to another delivery nozzle located on the other side of the patient interface 10a, which is clipped or glued in place near or over the other entrainment area. Because the oxygen delivery nozzles are connected in series, this arrangement requires that the holes of the nozzles and the cross section of the tube 602 be balanced in a way to ensure the same amount of oxygen flow is delivered by both nozzles. Along these lines, in the jet pump assemblies 106a of the patient interface 100a integrated into the patient circuit 10a, the jet nozzles 136a differ from the jet nozzles 136 of the jet pump assemblies 106 by virtue of the elimination of the low-pressure gas delivery lumen defining the above-described low-pressure jet nozzle inlet and outlet 140, 146. With this the elimination of the low-pressure gas delivery lumens in the jet nozzles 136a of the jet pump assemblies 106a, in the patient circuit 10a, second and third segments 404a, 406a of bi-lumen tubing 400a replace the second and third segments 404, 406 of tri-lumen tubing 400, as only two lumens within each segment 404, 406a are needed to effectuate high pressure gas delivery and pressure sensing fluid communication between the wye connector 300a and the patient interface 100a.

A further alternative arrangement is to have the two nozzles connected in parallel, so that two tubes depart from the oxygen connector 600 secured on the wye connector 300a of the patient interface 10a. This configuration is easier to pneumatically balance, though having additional tubing over both the first and second bi-lumen tubing segments 404a, 406a used to facilitate high pressure air/oxygen delivery and pressure sensing in the patient circuit 10a. The clip-on or glue-on nozzles are designed in a way to minimize the occlusion of the entrainment ports, so that the inspiratory and expiratory resistance values of the patient interface 10a can be retained unaltered. The delivery nozzles are also positioned in a way such that the oxygen flow is delivered in the zone between the nozzle and the throat of each of the jet pump assembles 106a. This position is considered optimal to minimize any positive pressure created by the oxygen flow and to maximize the amount of oxygen that is entrained and delivered to the patient. Clips and a modified cinch can also be included in the design to help manage the tube 602 and tubing segments 404a, 406a around the patients' face. The small portion of the tube 602 connecting the left and right oxygen nozzles in the series configuration is designed in a way that its presence does not interfere with the pillows of the patient interface 100a.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A multifunctional ventilator interface for selectively providing ventilation and continuous oxygen therapy to a patient, the multifunctional ventilator interface comprising:
   a first segment of tubing defining a high-pressure gas lumen, a low-pressure gas lumen, and a pressure sensing lumen that are isolated from each other within the tubing;
   a manifold housing defining a ventilation gas pathway;
   a jet pump housing coupled to the manifold housing and defining at least one entrainment port in fluid communication with ambient air;
   a jet nozzle cooperatively engaged to the jet pump housing, the jet nozzle defining a high-pressure jet nozzle outlet port operative to introduce gas from the high-pressure gas lumen into the ventilation gas pathway and to facilitate air entrainment through the at least one entrainment port and mixing of the entrained air with the gas concurrently introduced into the ventilation gas pathway;
   a nasal cannula defining a continuous oxygen therapy gas pathway; and
   a second segment of tubing fluidly coupling the low-pressure gas lumen of the first segment of tubing with the continuous oxygen therapy gas pathway of the nasal cannula.

2. The multifunctional ventilator interface of claim 1, wherein the jet nozzle further defines a low-pressure jet nozzle outlet port operative to introduce gas from the low-pressure gas lumen into the ventilation gas pathway, the low-pressure gas lumen branching from the first segment of tubing to define a first branch that extends within the second segment of tubing and a second branch that continues to the jet nozzle.

3. The multifunctional ventilator interface of claim 2, further comprising a wye connector for branching the low-pressure gas lumen from the first segment of tubing to define the first and second branches, the wye connector including a switch operative to toggle between blocking the first branch and blocking the second branch.

4. The multifunctional ventilator interface of claim 1, wherein the low-pressure gas lumen is bifurcated from the first segment of tubing without branching to extend within the second segment of tubing.

5. The multifunctional ventilator interface of claim 1, wherein the manifold housing further defines a pressure sensing pathway that fluidly communicates with a prescribed region of the ventilation gas pathway and is operative to be fluidly coupled to the pressure sensing lumen.

6. A system for selectively providing ventilation and continuous oxygen therapy to a patient, the system comprising:
   the multifunctional ventilator interface of claim 1; and
   a ventilator operable to provide ventilation gas to the jet nozzle via the high-pressure gas lumen of the first segment of tubing.

7. A multifunctional ventilator interface for selectively providing ventilation and continuous oxygen therapy to a patient, the multifunctional ventilator interface comprising:
   a first segment of tubing defining a high-pressure gas lumen, a low-pressure gas lumen, and a pressure sensing lumen that are isolated from each other within the tubing, the first segment of tubing terminating in a first quick connect fitting;
   a second segment of tubing defining a high-pressure gas lumen, the second segment of tubing terminating in a second quick connect fitting connectable to the first quick connect fitting to fluidly couple the high-pressure gas lumen of the first segment of tubing with the high-pressure gas lumen of the second segment of tubing;
   a third segment of tubing defining a low-pressure gas lumen, the third segment of tubing terminating in a third quick connect fitting connectable to the first quick connect fitting to fluidly couple the low-pressure gas lumen of the first segment of tubing with the low-pressure gas lumen of the third segment of tubing;
   a manifold housing defining a ventilation gas pathway;
   a jet pump housing coupled to the manifold housing and defining at least one entrainment port in fluid communication with ambient air;
   a jet nozzle cooperatively engaged to the jet pump housing and fluidly coupled to the high-pressure gas lumen of the second segment of tubing, the jet nozzle defining a high-pressure jet nozzle outlet port operative to introduce gas from the high-pressure gas lumen into the ventilation gas pathway and to facilitate air entrainment through the at least one entrainment port and mixing of the entrained air with the gas concurrently introduced into the ventilation gas pathway;
   a nasal cannula fluidly coupled to the low-pressure gas lumen of the third segment of tubing and defining a continuous oxygen therapy gas pathway in fluid communication with the low-pressure gas lumen.

8. The multifunctional ventilator interface of claim 7, wherein the second segment of tubing further defines a pressure sensing lumen, and the second quick connect fitting further fluidly couples the pressure sensing lumen of the first segment of tubing with the pressure sensing lumen of the second segment of tubing.

9. The multifunctional ventilator interface of claim 8, wherein the second segment of tubing further defines a low-pressure gas lumen, and the second quick connect fitting further fluidly couples the low-pressure gas lumen of the first segment of tubing with the low-pressure gas lumen of the second segment of tubing.

10. The multifunctional ventilator interface of claim 9, wherein the third quick connect fitting blocks the high-pressure gas lumen of the first segment of tubing.

11. The multifunctional ventilator interface of claim 10, wherein the third quick connect fitting further blocks the pressure sensing lumen of the first segment of tubing.

12. A system for selectively providing ventilation and continuous oxygen therapy to a patient, the system comprising:
the multifunctional ventilator interface of claim 7; and
a ventilator operable to provide ventilation gas to the jet nozzle via the high-pressure gas lumens of the first and second segments of tubing.

13. A multifunctional ventilator interface for selectively providing ventilation and continuous oxygen therapy to a patient, the multifunctional ventilator interface comprising:
tubing defining a high-pressure gas lumen, a low-pressure gas lumen, and a pressure sensing lumen that are isolated from each other within the tubing;
a manifold housing defining a gas pathway;
a jet pump housing coupled to the manifold housing and defining at least one entrainment port in fluid communication with ambient air;
a jet nozzle cooperatively engaged to the jet pump housing, the jet nozzle defining a high-pressure jet nozzle outlet port operative to introduce gas from the high-pressure gas lumen into the gas pathway and to facilitate air entrainment through the at least one entrainment port and mixing of the entrained air with the gas concurrently introduced into the gas pathway, the jet nozzle further defining a low-pressure jet nozzle outlet port operative to introduce gas from the low-pressure gas lumen into the gas pathway; and
a sleeve rotatably engaged to the jet pump housing, the sleeve including a first window and a second window selectively alignable with the at least one entrainment port by rotation of the sleeve relative to the jet pump housing, the first window being configured to allow ambient air to flow into the at least one entrainment port when at least partially aligned therewith, the second window being covered by a one-way valve configured to prevent ambient air from flowing into the at least one entrainment port but to allow exhalation out of the at least one entrainment port when the second window is at least partially aligned therewith.

14. The multifunctional ventilator interface of claim 13, wherein the second window is on the opposite side of the sleeve from the first window.

15. The multifunctional ventilator interface of claim 13, wherein the sleeve is prevented from assuming any rotational position in which patient exhalation cannot flow through the entrainment port.

16. A system for selectively providing ventilation and continuous oxygen therapy to a patient, the system comprising:
the multifunctional ventilator interface of claim 13; and
a ventilator operable to provide ventilation gas to the jet nozzle via the high-pressure gas lumen.

17. A multifunctional ventilator interface for selectively providing ventilation and continuous oxygen therapy to a patient, the multifunctional ventilator interface comprising:
tubing defining a high-pressure gas lumen, a low-pressure gas lumen, and a pressure sensing lumen that are isolated from each other within the tubing;
a manifold housing defining a gas pathway;
a jet pump housing coupled to the manifold housing and defining a one-way exhaust valve and at least one entrainment port in fluid communication with ambient air;
a jet nozzle cooperatively engaged to the jet pump housing, the jet nozzle defining a high-pressure jet nozzle outlet port operative to introduce gas from the high-pressure gas lumen into the gas pathway and to facilitate air entrainment through the at least one entrainment port and mixing of the entrained air with the gas concurrently introduced into the gas pathway, the jet nozzle further defining a low-pressure jet nozzle outlet port operative to introduce gas from the low-pressure gas lumen into the gas pathway; and
a sleeve rotatably engaged to the jet pump housing, the sleeve including a window selectively alignable with one of the at least one entrainment port and the one-way valve by rotation of the sleeve relative to the jet pump housing, the window being configured to allow ambient air to flow into the at least one entrainment port when at least partially aligned therewith and to allow the one-way exhaust valve to operate when at least partially aligned therewith.

18. The multifunctional ventilator interface of claim 17, wherein the one-way valve is on the opposite side of the jet pump housing from the at least one entrainment port.

19. The multifunctional ventilator interface of claim 17, wherein the sleeve is prevented from assuming any rotational position in which patient exhalation can flow neither through the at least one entrainment port nor through the one-way exhaust valve.

20. A system for selectively providing ventilation and continuous oxygen therapy to a patient, the system comprising:
the multifunctional ventilator interface of claim 17; and
a ventilator operable to provide ventilation gas to the jet nozzle via the high-pressure gas lumen.

\* \* \* \* \*